Figure 1:
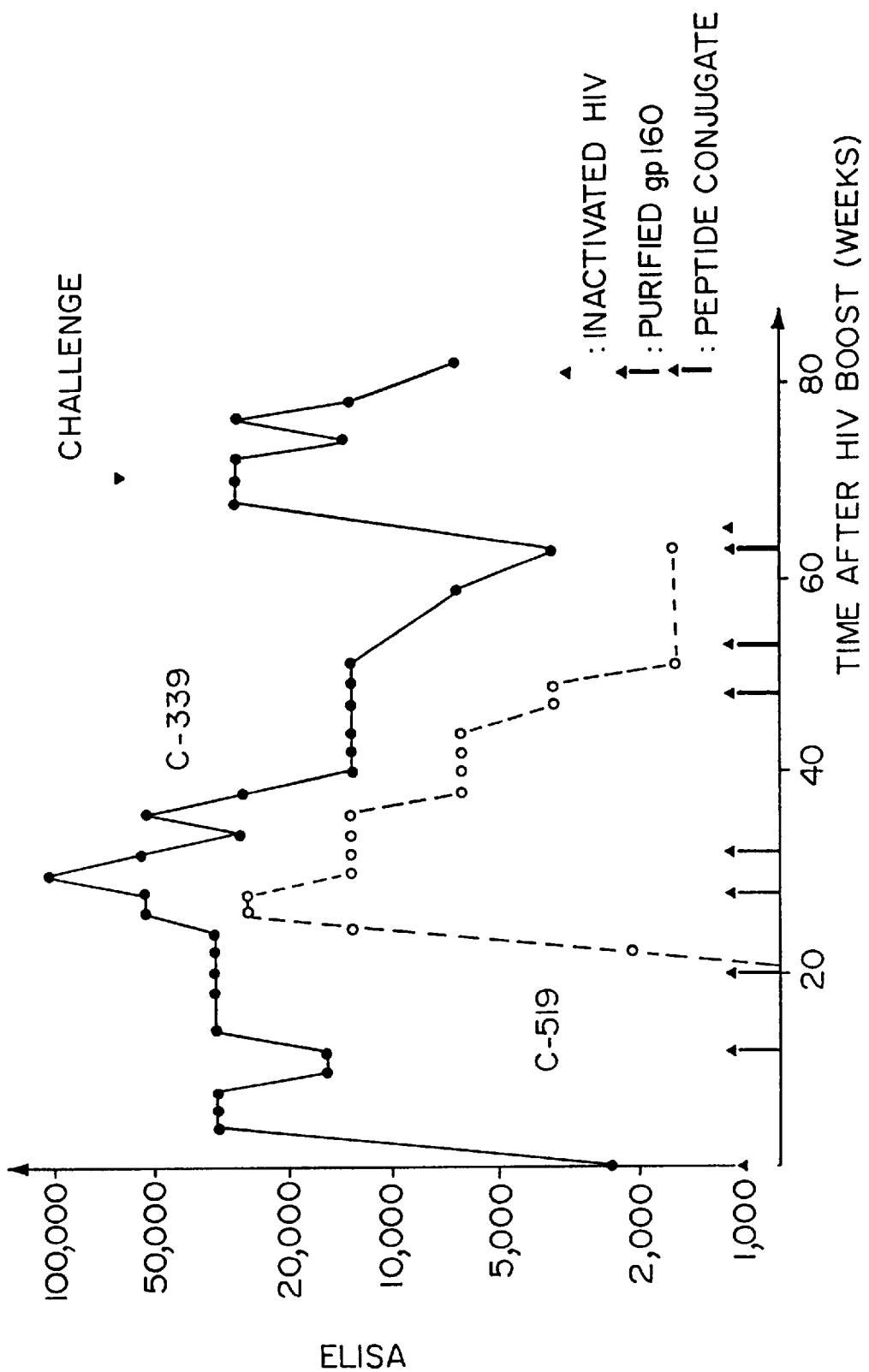

US005876724A

United States Patent [19]
Girard

[11] Patent Number: 5,876,724
[45] Date of Patent: Mar. 2, 1999

[54] INDUCTION OF NEUTRALIZING ANTIBODY AGAINST VIRAL INFECTION BY SYNERGY BETWEEN VIRUS ENVELOPE GLYCOPROTEIN AND PEPTIDES CORRESPONDING TO NEUTRALIZATION EPITOPES OF THE GLYCOPROTEIN

[75] Inventor: Marc Girard, Paris, France

[73] Assignee: Institut Pasteur, Paris, France

[21] Appl. No.: 266,448

[22] Filed: Jun. 28, 1994

Related U.S. Application Data

[63] Continuation of Ser. No. 145,664, Nov. 4, 1993, abandoned, which is a continuation of Ser. No. 782,241, Oct. 28, 1991, abandoned, which is a continuation-in-part of Ser. No. 672,647, Mar. 18, 1991, abandoned, which is a continuation-in-part of Ser. No. 494,749, Mar. 19, 1990, abandoned.

[51] Int. Cl.$^6$ .......................... A61K 39/21; A61K 38/16; A61K 38/00; C07K 1/00
[52] U.S. Cl. .................................... 424/188.1; 424/208.1; 424/204.1; 424/184.1; 530/324; 530/395; 514/8
[58] Field of Search .................... 424/188.1; 530/395; 514/8

[56] References Cited

U.S. PATENT DOCUMENTS

| 4,956,273 | 9/1990 | Kennedy et al. .......................... 435/5 |
| 5,013,548 | 5/1991 | Haynes et al. ....................... 424/188.1 |

FOREIGN PATENT DOCUMENTS

| 0227169 | 7/1987 | European Pat. Off. . |
| 0326109 | 8/1988 | European Pat. Off. . |
| 0317804 | 5/1989 | European Pat. Off. . |
| 0328403 | 8/1989 | European Pat. Off. . |
| WO 91/14449 | 10/1991 | WIPO . |

OTHER PUBLICATIONS

Haynes, 1993, "Scientific and Social Issues . . . " Science 260: 1279–1286.
Robey et al., 1986, "Prospect for prevention of . . . " PNAS 83: 7023–7027.
Neurath et al., 1990, "Confronting the hyper variability of an . . . " Molecular Immunology 27(6):539–549.
Gordon R. Dreesman et al., "Antibody to hepatitis B surface antigen after a single inoculation of uncoupled synthetic HBsAG peptides," Nature, vol. 295, Jan. 14, 1982, pp. 158–160.

Kemp B. Cease et al., "Helper T–cell antigenic site identification in the acquired immunodeficiency syndrome virus gp120 envelope protein using a 16–residue synthetic peptide," Proc. Natl. Acad. Sci. USA, vol. 84, Jun. 1987, pp. 4249–4253.

Jap Goudsmit et al., "Human immunodeficiency virus type 1 neutralization epitope with conserved architecture elicits early type–specific antibodies in experimentally infected chimpanzees," Proc. Natl. Acad. Sci. USA, vol. 85, Jun. 1988, pp. 4478–4482.

Robert Gallo et al., "HIV–HTLV gene nomenclature," Nature, vol. 333, Jun. 9, 1988, pp. 504–505.

Jay A. Berzofsky et al., "Antigenic peptides recognized by T lymphocytes from AIDS viral envelope–immune humans," Nature, vol. 334, Aug. 25, 1988, pp. 706–708.

Kashi Javaherian et al., "Principal neutralizing domain of the human immunodeficiency virus type 1 envelope protein," Proc. Natl. Acad. Sci. USA 86, Sep. 1989, pp. 6768–6772.

Beatrice Culmann et al., "An antigenic peptide of the HIV–1 NEF protein recognized by cytotoxic T lymphocytes of seropositive individuals in association with different HLA–B molecules," Eur. J. Immunol., vol. 19, 1989, pp. 2383–2386.

Karl Deres et al., "In vivo priming of virus–specific cytotoxic T lymphocytes with synthetic lipopeptide vaccine," Nature, vol. 342, Nov. 30, 1989, pp. 561–564.

Girard et al., Proc. Natl. Acad. Sci. USA, 88, 542–546 (1991).

Rusche et al., Proc. Natl. Acad. Sci. USA, 85, 3,198–3,202 (1988).

*Primary Examiner*—Lynette F. Smith
*Attorney, Agent, or Firm*—Finnegan, Henderson, Farabow, Garrett & Dunner

[57] ABSTRACT

The invention comprises a method of enhancing the immunogenicity of an envelope virus glycoprotein in a host organism. The method comprises administering to the host a composition comprising the virus envelope glycoprotein and at least one oligopeptide derived from the amino acid sequence of the envelope glycoprotein, wherein the oligopeptide contains or corresponds to virus-neutralization epitopes. The method and compositions are useful for vaccinating against viruses, such as HIV, SIV, HTLV-I, HTLV-II, or any retrovirus capable of inducing AIDS in its natural host.

33 Claims, 10 Drawing Sheets

1 2 3 4 5 6 7 8 9 10 11 12 13 14 15

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:1:

```
Tyr Asn Thr Arg Lys Ser Ile Arg Ile Gln Arg Gly Pro Gly Arg Ala
 1               5                  10                  15

Phe Val Thr Ile Gly Lys Ile Gly Asn
            20                  25
```

( 2 ) INFORMATION FOR SEQ ID NO:2:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:2:

```
Cys  Thr  Arg  Pro  Asn  Asn  Asn  Thr  Arg  Lys  Arg  Ile  Arg  Ile  Gln  Arg
1                   5                        10                       15
Gly  Pro  Gly  Arg  Ala  Phe  Val  Thr  Ile  Gly  Lys  Ile  Gly  Asn  Met  Arg
               20                       25                       30
Gln  Ala  His  Cys
               35
```

( 2 ) INFORMATION FOR SEQ ID NO:3:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:3:

```
Cys  Thr  Arg  Pro  Asn  Asn  Asn  Thr  Arg  Lys  Ser  Ile  Arg  Ile  Gln  Arg
1                   5                        10                       15
Gly  Pro  Gly  Arg  Ala  Phe  Val  Thr  Ile  Gly  Lys  Ile  Gly  Asn  Met  Arg
               20                       25                       30
Gln  Ala  His  Cys
               35
```

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:4:

```
Cys  Thr  Arg  Pro  Asn  Asn  Asn  Thr  Arg  Lys  Lys  Ile  Arg  Ile  Gln  Arg
1                   5                        10                       15
Gly  Pro  Gly  Arg  Ala  Phe  Val  Thr  Ile  Gly  Lys  Ile  Gly  Asn  Met  Arg
               20                       25                       30
Gln  Ala  His  Cys
               35
```

( 2 ) INFORMATION FOR SEQ ID NO:5:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:5:

```
Cys  Thr  Arg  Pro  Asn  Asn  Asn  Thr  Arg  Gly  Ser  Ile  Arg  Ile  Gln  Arg
1                   5                        10                       15

Gly  Pro  Gly  Arg  Ala  Phe  Val  Thr  Ile  Gly  Lys  Ile  Gly  Asn  Met  Arg
                    20                       25                       30

Gln  Ala  His  Cys
               35
```

( 2 ) INFORMATION FOR SEQ ID NO:6:

( i ) SEQUENCE CHARACTERISTICS:
        ( A ) LENGTH: 35 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:6:

```
Cys  Thr  Arg  Pro  Asn  Asn  Asn  Thr  Arg  Lys  Ser  Ile  Tyr  Ile  Gly  Pro
1                   5                        10                       15

Gly  Arg  Ala  Phe  His  Thr  Thr  Gly  Arg  Ile  Ile  Gly  Asp  Ile  Arg  Lys
                    20                       25                       30

Ala  His  Cys
          35
```

( 2 ) INFORMATION FOR SEQ ID NO:7:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:7:

```
Cys  Thr  Arg  Pro  Tyr  Asn  Asn  Val  Arg  Arg  Ser  Leu  Ser  Ile  Gly  Pro
1                   5                        10                       15

Gly  Arg  Ala  Phe  Arg  Thr  Arg  Glu  Ile  Ile  Gly  Ile  Ile  Arg  Gln  Ala
                    20                       25                       30

His  Cys
```

( 2 ) INFORMATION FOR SEQ ID NO:8:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:8:

```
Cys  Thr  Arg  Pro  Gly  Asn  Asn  Thr  Arg  Arg  Gly  Ile  His  Phe  Gly  Pro
1                   5                        10                       15

Gly  Gln  Ala  Leu  Tyr  Thr  Thr  Gly  Ile  Val  Gly  Asp  Ile  Arg  Arg  Ala
                    20                       25                       30

Tyr  Cys
```

( 2 ) INFORMATION FOR SEQ ID NO:9:

( i ) SEQUENCE CHARACTERISTICS:
        ( A ) LENGTH: 34 amino acids
        ( B ) TYPE: amino acid
        ( C ) STRANDEDNESS:

(D) TOPOLOGY: Not Relevant (ii) MOLECULE TYPE: peptide (xi) SEQUENCE DESCRIPTION: SEQ ID NO:9:

Cys Ala Arg Pro Tyr Gln Asn Thr Arg Gln Arg Thr Pro Ile Gly Leu
1               5                   10                  15
Gly Gln Ser Leu Tyr Thr Thr Arg Ser Arg Ser Ile Ile Gly Gln Ala
            20                  25                  30
His Cys (2) INFORMATION FOR SEQ ID NO:10:

(i) SEQUENCE CHARACTERISTICS:
    (A) LENGTH: 35 amino acids
    (B) TYPE: amino acid
    (C) STRANDEDNESS:
    (D) TOPOLOGY: Not Relevant (ii) MOLECULE TYPE: peptide (xi) SEQUENCE DESCRIPTION: SEQ ID NO:10:

Cys Thr Arg Pro Asn Asn Asn Thr Arg Lys Ser Ile Thr Lys Gly Pro
1               5                   10                  15
Gly Arg Val Ile Tyr Ala Thr Gly Gln Ile Ile Gly Asp Ile Arg Lys
            20                  25                  30
Ala His Cys
         35

(2) INFORMATION FOR SEQ ID NO:11:

(i) SEQUENCE CHARACTERISTICS:
    (A) LENGTH: 35 amino acids
    (B) TYPE: amino acid
    (C) STRANDEDNESS:
    (D) TOPOLOGY: Not Relevant (ii) MOLECULE TYPE: peptide (xi) SEQUENCE DESCRIPTION: SEQ ID NO:11:

Cys Thr Arg Pro Asn Asn Asn Thr Arg Lys Arg Ile Thr Met Gly Pro
1               5                   10                  15
Gly Arg Val Tyr Tyr Thr Thr Gly Gln Ile Ile Gly Asp Ile Arg Arg
            20                  25                  30
Ala His Cys
         35

(2) INFORMATION FOR SEQ ID NO:12:

(i) SEQUENCE CHARACTERISTICS:
    (A) LENGTH: 35 amino acids
    (B) TYPE: amino acid
    (C) STRANDEDNESS:
    (D) TOPOLOGY: Not Relevant (ii) MOLECULE TYPE: peptide (xi) SEQUENCE DESCRIPTION: SEQ ID NO:12:

Cys Thr Arg Pro Gly Ser Asp Lys Arg Gln Ser Thr Pro Ile Gly Leu
1               5                   10                  15
Gly Gln Ala Leu Tyr Thr Thr Arg Gly Arg Thr Lys Ile Ile Gly Gln
            20                  25                  30
Ala His Cys
         35

( 2 ) INFORMATION FOR SEQ ID NO:13:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:13:

```
Cys Thr Arg Pro Gly Ser Asp Lys Lys Ile Arg Gln Ser Ile Arg Ile
1               5                   10                  15
Gly Pro Gly Lys Val Phe Tyr Ala Lys Gly Gly Ile Thr Gly Gln Ala
                20                  25                  30
His Cys
```

( 2 ) INFORMATION FOR SEQ ID NO:14:

( i ) SEQUENCE CHARACTERISTICS:
        ( A ) LENGTH: 35 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:14:

```
Cys Thr Arg Pro Asn Asn Asn Thr Lys Lys Gly Ile Ala Ile Gly Pro
1               5                   10                  15
Gly Arg Thr Leu Tyr Ala Arg Glu Lys Ile Ile Gly Asp Ile Arg Gln
                20                  25                  30
Ala His Cys
        35
```

( 2 ) INFORMATION FOR SEQ ID NO:15:

( i ) SEQUENCE CHARACTERISTICS:
        ( A ) LENGTH: 35 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:15:

```
Cys Thr Arg Pro Asn Asn His Thr Arg Lys Arg Val Thr Leu Gly Pro
1               5                   10                  15
Gly Arg Val Trp Tyr Thr Thr Gly Glu Ile Leu Gly Asn Ile Arg Gln
                20                  25                  30
Ala His Cys
        35
```

( 2 ) INFORMATION FOR SEQ ID NO:16:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:16:

```
Cys Thr Arg Pro Gly Asn Asn Thr Arg Arg Gly Ser His Phe Gly Pro
1               5                   10                  15
```

```
        Gly  Gln  Ala  Leu  Tyr  Thr  Thr  Gly  Ile  Val  Gly  Asp  Ile  Arg  Arg  Ala
                       20                       25                       30

Tyr  Cys
```

( 2 ) INFORMATION FOR SEQ ID NO:17:

( i ) SEQUENCE CHARACTERISTICS:
        ( A ) LENGTH: 35 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:17:

```
        Cys  Thr  Arg  Pro  Asp  Asn  Lys  Ile  Thr  Ser  Arg  Gln  Thr  Pro  Ile  Gly
        1                   5                        10                       15

Leu  Gly  Gln  Ala  Leu  Tyr  Thr  Thr  Arg  Ile  Lys  Gly  Asp  Ile  Arg  Gln
                       20                       25                       30

Ala  Tyr  Cys
                  35
```

( 2 ) INFORMATION FOR SEQ ID NO:18:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:18:

```
        Cys  Thr  Arg  Pro  Asn  Asn  Asn  Val  Arg  Arg  His  Ile  His  Ile  Gly
        1                   5                        10                       15

Pro  Gly  Arg  Ala  Phe  Tyr  Thr  Gly  Glu  Ile  Arg  Asn  Ile  Arg  Gln  Ala
                       20                       25                       30

His  Cys
```

( 2 ) INFORMATION FOR SEQ ID NO:19:

( i ) SEQUENCE CHARACTERISTICS:
        ( A ) LENGTH: 33 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:19:

```
        Cys  Thr  Arg  Pro  Tyr  Lys  Asn  Thr  Arg  Gln  Ser  Thr  Pro  Ile  Gly  Leu
        1                   5                        10                       15

Gly  Gln  Ala  Leu  Tyr  Thr  Thr  Arg  Thr  Lys  Ser  Ile  Gly  Gln  Ala  His
                       20                       25                       30

Cys
```

( 2 ) INFORMATION FOR SEQ ID NO:20:

( i ) SEQUENCE CHARACTERISTICS:
        ( A ) LENGTH: 35 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:20:

Cys Thr Arg Pro Asn Asn Asn Thr Thr Arg Ser Ile His Ile Gly Pro
1               5                   10                  15

Gly Arg Ala Phe Tyr Ala Thr Gly Asp Ile Ile Gly Thr Ile Arg Gln
            20                  25                  30

Ala His Cys
        35

( 2 ) INFORMATION FOR SEQ ID NO:21:

( i ) SEQUENCE CHARACTERISTICS:
      ( A ) LENGTH: 35 amino acids
      ( B ) TYPE: amino acid
      ( C ) STRANDEDNESS:
      ( D ) TOPOLOGY: Not Relevant ( i i ) MOLECULE TYPE: peptide ( x i ) SEQUENCE DESCRIPTION: SEQ ID NO:21:

Cys Thr Arg Pro Asn Tyr Asn Lys Arg Lys Arg Ile His Ile Gly Pro
1               5                   10                  15

Gly Arg Ala Phe Tyr Thr Thr Lys Asn Ile Ile Gly Asp Ile Arg Gln
            20                  25                  30

Ala His Cys
        35

( 2 ) INFORMATION FOR SEQ ID NO:22:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: other nucleic acid ( x i ) SEQUENCE DESCRIPTION: SEQ ID NO:22:

GCTTCTAGAT AATACAGTAG CAACCCTCTA TTG                33

( 2 ) INFORMATION FOR SEQ ID NO:23:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: other nucleic acid ( x i ) SEQUENCE DESCRIPTION: SEQ ID NO:23:

GTCGGCCTTA AAGGCCCTGG GGCTTGTTCC ATCTATC            37

INDUCTION OF NEUTRALIZING ANTIBODY AGAINST VIRAL INFECTION BY SYNERGY BETWEEN VIRUS ENVELOPE GLYCOPROTEIN AND PEPTIDES CORRESPONDING TO NEUTRALIZATION EPITOPES OF THE GLYCOPROTEIN

CROSS-REFERENCE TO RELATED APPLICATION

This application is a continuation of application Ser. No. 08/145,664, filed Nov. 4, 1993, now abandoned, which is a continuation of application Ser. No. 07/782,241, filed Oct. 28, 1991, now abandoned, which is a continuation-in-part of application Ser. No. 07/672,647, filed Mar. 18, 1991, now abandoned, which is a continuation-in-part of application Ser. No. 07/494,749, filed Mar. 19, 1990, now abandoned.

BACKGROUND OF THE INVENTION

This invention relates to a vaccination process, which involves the simultaneous or consecutive use of a priming antigen, in this case the glycoprotein from a virus, such as HIV, SIV or any lentivirus capable of inducing AIDS in its natural host, or from an HTLV-I or HTLV-II type retrovirus, and an amplifying composition comprised of synthetic oligopeptides, which are free or bound to a carrier molecule, and in which the oligopeptides correspond to the neutralization epitopes for this same glycoprotein. This invention also relates to a composition for use in the process.

An effective vaccine composition against viruses must produce rapid neutralization of the viruses in order to prevent the viruses from possibly protecting themselves in a latent provirus form within the chromosomes of resting cells or from finding refuge in the cellular or tissue compartments where they would be beyond the reach of the immune system.

From previous experiments conducted with both chimpanzees in the case of HIV and macaques in the case of SIV, it is clear that inoculation of virus envelope glycoprotein alone does not make it possible to obtain a fully protective immune response. In particular, the virus envelope glycoprotein does not produce a sufficient level of neutralizing antibodies in order to provide protection against infection.

Accordingly, there exists a need in the art for a method of inducing a sufficient level of neutralizing antibodies against virus infection in a host susceptible to the infection by the virus. In addition, there exists a need in the art for a pharmaceutical composition for use in the method.

SUMMARY OF THE INVENTION

This invention aids in fulfilling these needs in the art. An object of this invention is to reinforce the immunogenicity of at least one envelope glycoprotein of a virus by combining the glycoprotein with at least one peptide, and preferably at different times a group of peptides, derived from the sequence of the envelope glycoprotein and corresponding to virus-neutralization epitopes, i.e. corresponding to amino acid sequences involved in the production of neutralizing antibodies in the host to which they are administered.

Accordingly, this invention provides a method of enhancing the immunogenicity of an envelope glycoprotein of a virus in a host and a composition for use in this method. The method comprises administering to the host at least one envelope glycoprotein of the virus and at least one peptide derived from the amino acid sequence of the envelope glycoprotein. The peptide comprises at least one virus-neutralization epitope. The envelope glycoprotein and the peptide are administered in an amount sufficient to induce neutralizing antibodies in the host.

The invention provides a composition for enhancing the immunogenicity of an envelope glycoprotein of a determined virus, wherein the composition comprises as a combined preparation for simultaneous, separate, or sequential use:

(A) at least one envelope glycoprotein of the virus or a fragment of at least 50 amino acids of the glycoprotein and, (B) at least one peptide derived from the amino acid sequence of the envelope glycoprotein, and wherein the peptide comprises at least one virus-neutralization epitope, and wherein the envelope glycoprotein and the peptide are administered in an amount sufficient to induce neutralizing antibodies in the host.

For the purpose of the invention, the word "composition" is intended to comprise combined preparation in which the components—in this case the envelope glycoprotein and the peptide or peptides derived from the envelope glycoprotein—can be presented in a mixture or can be presented side-by-side and therefore be applied simultaneously, separately or at intervals, to the host. For instance, the peptide(s) present in the composition can be maintained separated from other components in order to be administered sequentially to booster the immunogenic reaction which is primed with the envelope glycoprotein.

In a preferred embodiment, the invention provides a composition which comprises the above envelope glycoprotein and peptide providing the envelope glycoprotein is present in an amount sufficient for priming the induction of neutralizing antibodies in a host to which it is administered, and the at least one peptide is in an amount sufficient to enhance the induction of persistent neutralizing antibodies in the host to which it is administered.

Accordingly, the invention concerns the use of at least one of the above described peptides for enhancing the immunogenicity of an envelope glycoprotein of a virus, when this glycoprotein is administered to a host to induce neutralizing antibodies.

The composition of the invention can be used for the preparation of an immunotherapeutic drug. In this case the composition is administered to seropositive people in order to increase the level of neutralizing antibodies and accordingly to enable a control of the virus.

Methods are described by J. Salk in "4° Colloque des Cent Gardes—Retroviruses of human AIDS and related animal diseases—Ed. M. Girard, L. Valette—Foundation Merieux—1990 p. 273–278" and in "Nature 1989, vol. 327, p. 473–476".

This invention also provides a composition for vaccinating a host against infection by a virus. The composition comprises at least one envelope glycoprotein of the virus in an amount sufficient for priming vaccination in a host to which the envelope glycoprotein is administered. The composition also contains at least one peptide derived from the amino acid sequence of the envelope glycoprotein. The peptide comprises at least one virus-neutralization epitope of the glycoprotein. The composition contains the peptide in an amount sufficient to enhance the induction of persistent neutralizing antibodies in the host.

The description of the invention in connection with the use as vaccine of the defined composition can also be applied to the use as immunotherapeutic drug of this composition, provided that the described means enables the enhancement of the production of neutralizing antibodies.

Peptides and envelope glycoproteins can be combined under conditions allowing them to interact by non-covalent physical combination or by covalent chemical bonding. Alternatively, and in a preferred embodiment of the invention, a priming vaccination (priming) is achieved by injections of envelope glycoprotein, with protective immunity being subsequently enhanced by the injection of immunogenic peptides corresponding to the neutralization epitopes.

Two of three immunized chimpanzees were successfully protected against virus infection and virus was suppressed in a third animal for a long period using the compositions and methods of this invention. These results demonstrate that this invention makes it possible to elicit protection against HIV-1 through immunization.

BRIEF DESCRIPTION OF THE DRAWINGS

This invention will be more fully described by reference to the following Figures in which:

FIG. 1 depicts anti-HIV antibody level measured by ELISA (Genetic Systems Kit) in chimpanzee FUNFACE (C-339) and a control (C-519). The results are shown as serum ELISA titre (1:dilution giving positive response) versus time. Time zero in the Figure corresponds to the day of the first booster with inactivated HIV. The animal was challenged at 70 weeks (arrow).

FIG. 2 depicts neutralizing antibody level in chimpanzees FUNFACE (dark circles) and ROBERT (open circles) in response to the injection of a KLH-BRU peptide conjugate (arrows). The animals were inoculated at 0, 3, and 19 weeks (arrows) and challenged at 24 weeks.

FIG. 3 depicts anti-HIV antibody levels measured by ELISA in chimpanzee ROBERT (C-433). The results are shown as serum ELISA titre (1:dilution giving positive response) versus time. Time zero corresponds to the day of the first antigen injection (gp160env, p27nef, p23vif, and p18gag). The animal was challenged at 84 weeks (arrow).

FIG. 4 depicts neutralization of HIV-1 BRU as a function of the serum dilution in chimpanzees JOJOTOO (499), IRA (151), and HENRY II (531) at time t0 (▣) and at 2 weeks (□) and 5 weeks (♦) after a third inoculation of free peptides.

FIG. 5 depicts neutralization of HIV-1 BRU (dotted curves) and HIV-1 ARV-2 (solid curves) as a function of the serum dilution in chimpanzee JOJOTOO (C-499) at time t0 (▣) and after the third inoculation of free peptides (♦).

FIGS. 6A–C show total HIV-1-specific antibody titers for chimpanzees C-339 (A), C-433 (B), and C-499 (C). At the indicated times, chimpanzees were inoculated with various immunogens (see Table 1) or challenged with HIV-1. Titers are defined as the reciprocal of the highest dilution of serum that was positive using an HIV-1 EIA kit (Genetic Systems).

FIG. 7 depicts neutralizing antibody titers in serum from C-339, C-433 and C-499 during immunization with HIV-1 antigens. Titers are the reciprocal of the highest dilution of serum that gave 90% reduction in number of syncytia formed by CEM-SS cells (Nara, P. L., Hatch, W. C., Dunlop, N. M., Robey, W. G., Arthur, L. O., Gonda, M. A. & Fischinger, P. J. (1987) *AIDS Res. Human Retroviruses* 3, 283–302.) when compared to that obtained with control serum from a naive chimpanzee.

FIG. 8 shows PCR analysis of DNA from PBMC and lymph node tissue obtained 6 months after challenge of chimpanzees C-339 and C-433 with HIV-1.

(A) Ethidium bromide-stained gel of amplified HIV sequences following two rounds of PCR with nested sets of primers. The size of the HIV-specific amplified fragment is 141 base pairs.

Lane 1, 0.5 $\mu$g of OX174 DNA cleaved with HaeIII as molecular weight markers.

Lanes 2–7, positive controls for sensitivity, each containing tenfold fewer molecules of pHXB2 cleaved with XbaI than the previous sample, starting with 3000 molecules in lane 2. Each sample was amplified in the presence of 1 $\mu$g DNA (the amount of DNA in $1.5\times10^5$ cells) from an uninfected control chimpanzee, C-519. One negative control sample (lane 14) was identified and used as a source of uninfected chimpanzee cellular DNA; all other samples were tested blindly. C-487 was an HIV-1 infected chimpanzee, used as a positive control.

Lanes 8–11, DNA from PBMC of C-339, C-487, C-433 and C-519, respectively.

Lanes 12–15, DNA from lymph node tissue of C-487, C-433, C-519 and C-339, respectively.

(B) Ethidium bromide-stained gel of an amplified portion of the beta-globin gene (Scharf, S. J., Horn, G. T. & Erlich, H. A. (1986) *Science* 233, 1076–1078), as an internal control. (C) Oligonucleotide hybridization of PCR-amplified sequences. PCR reaction products shown in (A) were denatured and annealed with [$^{32}$P]-labeled primer SK102, which anneals entirely within the amplified sequence; the products were examined following polyacrylamide gel electrophoresis and authoradiography according to Kwok and Kellogg (Kwok, S. & Kellogg, D. E. (1990) in *PCR Protocols: A Guide to Methods and Applications*: eds. Innis, M. A., Gelfand, D. H., Sninsky, J. J. & White T. J. (Academic Press, Inc., San Diego, Calif.) pp. 337–347).

FIG. 9 depicts immunoblot analysis of antibodies to specific HIV-1 proteins following immunization and challenge of chimpanzees C-433, C-339 and C-499. Serum samples were diluted 1:200 and tested with a commercial kit (Diagnostics Pasteur). For the samples shown, sera were collected one month prior to challenge (marked by arrow) and then at 4 week intervals. Molecular weights of HIV-1 proteins are shown for positive control serum.

FIG. 10 shows anti-gp160 ELISA titers in Rhesus monkeys treated according to the invention.

FIG. 11 shows anti-V3 BRU antibody titers in Rhesus monkeys treated according to the invention.

BEST MODE FOR CARRYING OUT THE INVENTION

Previous attempts to protect chimpanzees against HIV infection by vaccination have failed, despite the use of several different types of vaccines: synthetic peptides, live recombinant vaccinia virus (VV) expressing HIV antigens, native or recombinant gp120 or gp160 envelope antigens, and inactivated whole virus. The failure to protect a chimpanzee against an infectious HIV challenge by prior vaccination with recombinant VV followed by formalin- and betapropiolactone-inactivated whole HIV was previously reported.

This failure led to two considerations on which the present approach is based:

1—Protection against infection with cell-free HIV probably requires high levels of neutralizing antibodies (Ab). Should the virus escape eradication by neutralizing Ab or antibody dependent cellular cytoxicity (ADCC), the virus could easily remain sheltered from the immune system, either as an integrated provirus and/or by infection of cells in the bone marrow or central nervous system. Replication of the virus, even if limited, could lead to the early emergence of neutralization escape mutants. Therefore, rapid neutralization of the challenge virus may be a key to successful vaccination.

2—Up to 1990, induction of neutralizing Ab by all the vaccines tested in chimpanzees has been at best mediocre. This may explain their failure to protect the animals against infection. To be efficacious, a vaccine, therefore, should induce higher neutralizing Ab titers than those obtained so far.

It was, therefore, sought to elicit the highest possible neutralizing Ab titers in chimpanzees through successive immunization protocols using a variety of immunogens.

One chimpanzee, C-339, was immunized initially with four injections (at 0, 1, 2 and 6 months) of 250 μg of formalin and betapropiolactone-inactivated whole HIV mixed with SYNTEX ADJUVANT FORMULATION™ (SAF-1), using a concentration of 1 mg threonyl MDP. The animal developed high HIV ELISA titers (1:200,000, using the ELAVIA™ kit from Diagnostic Pasteur with a cut off of 0.1) and showed strong reactivity by Western blot to gp160, gp120, and gp41 env, and to p55, p40, p25, and p18gag. Its neutralizing Ab titers reached 1:400 and 1:64, respectively, using two different neutralization assays; the first assay scored for 50% inhibition of immunofluorescent foci formation on MT4 cells, and the second one for 90% inhibition of syncytia formation on CEM-SS cells. Using a more stringent assay (100% inhibition of reverse transcriptase production in fresh human PBL), the maximum titer of neutralizing Ab was 1:160, obtained immediately after the booster injection. These titers, however, did not persist, but quickly declined to lower levels.

In an attempt to increase the neutralizing Ab titers of chimpanzee C-339, the animal was boosted repeatedly with recombinant soluble gp160env purified from the supernatant of BHK-21 cell cultures infected with VV-1163, a VV-env recombinant expressing a gp160 molecule containing a deletion of the transmembrane domain and a modification by site-directed mutagenesis of the gp120/gp41 cleavage site to prevent cleavage. Vaccinia virus VV-1163 can be made using the procedures described by Kieny et al., Protein Engineering 2:219–226 (1988). The antigen was purified by sequential lectin and cation-exchange chromatography, then was injected I.D. at multiple sites of the chest (125–150 μg per injection) with a human dose of BCG. This was followed by 3 successive I.M. injections of the antigen formulated with SAF-1™. ELISA and neutralizing Ab titers were followed on routinely; however, both remained unchanged during and after this course of immunizations.

Failure of the gp160env to enhance antibody responses was not due to lack of immunogenicity, as shown by immunizing in parallel a naive chimpanzee, C-519, which previously had not been exposed to HIV antigens. Using the same immunization protocol as for C-339, C-519 readily developed a strong anti-gp160 Ab response, and its ELISA titer reached 200,000 after two injections. Therefore, failure of C-339 to respond to the injections of gp160env was not due to lack of potency of the immunogen, but most likely to some unidentified, immunological block in the animal. It was reasoned that such an impairment might be by-passed by injecting the animal with only those epitopes of the gp120 molecule that were required for induction of neutralizing Ab.

It has been shown that HIV neutralizing Ab are primarily directed against the type-specific, hypervariable loop from the V3 region of gp120. Therefore, using bisdiazobenzidine, a 25-mer oligopeptide with the sequence of that loop 4(SEQ ID NO:1)-(YNTRKSIRIQRGPGRAFVTIGKIGN) from the HIV-I BRU (IIIb) strain was cross-linked to KLH. C-339 was injected with the peptide-carrier conjugate in the presence of SAF-1™ (300 μg of peptide) at 0, 3, and 19 weeks. No increase in ELISA titer was observed, but sustained neutralizing Ab titers were obtained following the second injection. The animal was challenged on week 26 (see below), together with another chimpanzee, ROBERT, C-433, that had undergone a parallel, albeit distinct, course of immunization.

Chimpanzee C-433 had been primed with VV-1139, a VV recombinant expressing the same uncleaved version of gp160env as VV-1163, but containing the transmembrane domain. Vaccinia virus VV-1139 can be made using the procedures described by Kieny et al., Protein Engineering 2:219–226 (1988). Scarification was done with $2\times10^8$ PFU of the VV recombinant and was repeated at 4 and 22 weeks. The animal was then immunized with 125–150 μg each of recombinant soluble gp160, purified as described above, and recombinant p18gag, p27nef and p23vif (purified from *E. coli*) mixed with SAF. Injections were at 0, 1, 2, and 6 months, and resulted in an ELISA Ab titer of 1:400,000. Again, however, neutralizing Ab titers remained low (1:400 and 1:128, by the immunofluorescent focus and syncytia-forming assays, respectively). C-433, therefore, was injected with the same V3 peptide-KLH conjugate, according to the same immunization protocol, as C-339. The neutralizing Ab titer of C-433 was immediately boosted several fold and the animal was challenged in parallel with C-339.

The two chimpanzees were challenged using a titrated virus stock (III B stock, lot No. 40) from the National Cancer Institute (a kind gift of Larry Arthur, NCI, Frederick, Md.). The stock, which contained $10^4$ TCID50/ml, was diluted 1:100, and 1 ml of the dilution was injected I.V. into both of the immunized animals. To prevent unnecessary use of an animal, and in view of the fact that the virus stock had been titrated twice in chimpanzees and its infectivity for chimpanzees had been assessed regularly, no control naive chimp was used in this experiment. The chimp ID50 of this virus stock was equivalent to 4 TCID50, and in two experiments, injection of chimpanzees with 40 TCID50 resulted in the appearance of detectable virus in PBL as early as 2 weeks after injection and was followed by seroconversion at 4 weeks.

By contrast, the challenge of chimpanzees C-339 and C-433 with 100 TCID50 was not followed by detectable increases in antibody titers during the 24 weeks that have elapsed since time of challenge. In addition, C-433 has not developed anti-p25gag Ab, C-339 has not developed anti-p27nef Ab, nor have the 2 animals developed anti-p66pol Ab.

PCR tests done at 6 weeks, 12 weeks, and 24 weeks after challenge on PBL from both chimpanzees were negative, whereas the insufficiently immunized chimpanzee (C-487) that was challenged and became infected a year ago, was positive by PCR. Finally, virus has not been recovered by cocultivation of PBL from either C-339 or C-433 with human PBL, as judged by absence of RT activity after 6 weeks of culture.

It is understood that the expression "neutralization epitopes" is taken to mean, in the case of HIV-1, the major virus-neutralization epitope, such as described, among others, by Putney et al. in 1986 (Science 234:1392–1395) and by Rusche et al. in 1988 (Proc. Natl. Acad. Sci. USA 85:3198–3202), for which the sequence corresponds approximately to amino acids 296 to 331 of the HIV-1 envelope glycoprotein as described in the work of Myers et al. (Human Retroviruses and AIDS 1989, Los Alamos, Natl. Lab). Also covered by the invention are peptides corresponding to equivalent regions of different variants of HIV-1, or another retrovirus, HIV-2, HTLV-I, or HTLV-II in humans, FIV, FeLV, or another lentivirus in animals, and which correspond to the neutralization epitopes of the virus under consideration.

Also included in the scope of the invention are peptides corresponding to those known as minor neutralization epitopes, characterized by the fact that they belong to conserved regions of the envelope glycoprotein, and that they induce antibodies capable of neutralizing, at relatively low titers, several different isolates of the virus under consideration, for example several different isolates of HIV-1, or even different isolates of HIV-1, and also of HIV-2. An example of a minor epitope can be found in the work of Chanh et al. in 1986 (The EMBO Journal, 5:3065–3071) and in that of Evans et al. in 1989 (Nature 339:385–388), or Almond et al. in "Retroviruses of human AIDS and related animal disease," M. Girard and L. Valette, Foundation Marcel Merieux, Lyon, 1990, in press).

Immunogenic peptides of major and minor neutralization epitopes are preferably mixed with each other to ensure the greatest possible protection. They can be administered in the free state, not coupled to a carrier molecule. They can also be combined with a sequence of amino acids having one or preferably several T-epitopes from one or several structural or non-structural proteins of the same retrovirus or a retrovirus immunologically cross-reactive with the former, particularly such as described in French patent application of Girard-Gluckman-Bahraoui, No. 89.11044 of Aug. 18, 1989.

In one particularly preferred embodiment of the invention, immunogenic peptides corresponding to neutralization epitopes are chemically coupled to sequences of amino acids corresponding to T-epitopes. In another case, the peptides are coupled to a carrier molecule which bears the desired T-epitopes, by allowing them to react, for example, with a bifunctional reagent or any other coupling agent desired.

As a carrier molecule, any protein coded for by the viral genome can be used (in the case of HIV, the proteins produced by tat, rev, vif, pol, vpr, vpx, vpu, gag, env, or nef genes), or other (protein-type) molecules, such as HBs antigen, HBc antigen, tetanus toxoid, hemocyanin, human albumin, or polypeptides (for example polylysine) or appropriate lipopeptides.

In a particular embodiment of the invention in which the envelope glycoprotein molecules and major and minor neutralizing peptides (either free or bound to carrier molecules) are combined in the same vaccine preparation, the priming effect of the envelope glycoproteins appears after the first one or few injections of vaccine, and the amplification effect due to peptides immediately afterward.

Thus, an object of the invention is to use a first antigen, in this case the several envelope glycoproteins of each of the retrovirus serotypes under consideration, which has the effect of priming the response of the immune system; and a second antigen, in this case the synthetic peptides corresponding to major and also possibly minor neutralization epitopes of the different serotypes of the virus under consideration, for vaccination (preferably consecutively, but in a mixture, if necessary) with the purpose of amplifying and consolidating the initial response, particularly through induction of long-lasting, high-titer neutralizing antibodies. This invention makes it possible to induce immunity that persists as long as about six months and even as long as one year or more.

The glycoproteins used to prime the response of the immune system are preferably whole molecules as obtained before possible cleavage. Thus, in the case of HIV-1, gp160 is preferable to gp120, and the same is true for other retroviruses. This allows anti-gp41 antibodies in particular to be induced, which is a favorable sign in virus carriers (Klasse et al., Proc. Natl. Acad. Sci. USA, 85:5225–5229).

The peptides constituting the "amplifier" can be free or physically bound (especially by hydrophobic bonding) or chemically bound (especially by covalent bonding) to carrier molecules. They can also be associated with other peptides corresponding to T-epitopes, or even to peptides, lipopeptides, glycopeptides, aliphatic chains, fatty acids, or any combination of these capable of stimulating the immune system and/or specifically targeting the "amplifier" peptides to antigen-presenting cells.

From this point of view, a particularly advantageous presentation of peptides corresponding to HIV neutralization epitopes is to bind them, preferably by covalent chemical bonding, to an aliphatic sequence, particularly as described in 1989 by Deres et al. (Nature 342:561–564). The amplifying peptides presented in this way can induce not only a B-cell response, but also a CTL $CD8^+$ response, restricted HLA Class I, as described by Takanashi et al. in 1988 (Proc. Natl. Acad. Sci. USA 85:3105–3109).

When the virus has a high degree of antigenic variability, as in the case of HIV-1 and HIV-2, it is necessary to use as priming antigen not just one, but several envelope glycoproteins with different sequences, each sequence corresponding to an isolate or group of isolates of the virus under consideration, so as to obtain as many priming phenomena as desired, since each is specific for a single isolate or group of isolates. In this case, it is understood that the amplifying peptides are composed of the mixture of neutralization peptides of each of the isolates under consideration, as indicated below.

A preparation of HIV-1 amplifier peptides according to the invention is characterized by the fact that it contains at least one of the sequences or one part of the sequences described below in one letter amino acid code:

(SEQ ID NO:2) C-TRPNNNTRKR IRIQRGPGRA FVTIGK-IGN M-RQAH-C (SEQ ID NO:3) C-TRPNNNTRKS IRIQRGPGRA FVTIGK-IGN M-RQAH-C (SEQ ID NO:4) C-TRPNNNTRKK IRIQRGPGRA FVTIGK-IGN M-RQAH-C (SEQ ID NO:5) C-TRPNNNTRGS IRIQRGPGRA FVTIGK-IGN M-RQAH-C (SEQ ID NO:6) C-TRPNNNTRKS IYI--GPGRA FHTT-GRIIGD -IRKAH-C (SEQ ID NO:7) C-TRPYNNVRRS LSI--GPGRA FRTRE-IIGI -IRQAH-C (SEQ ID NO:8) C-TRPGNNTRRG IHF--GPGQA LYTTGIV-GD -IRRAY-C (SEQ ID NO:9) C-ARPYQNTRQR TPI--GLGQS LYTTRSR-SI -IGQAH-C (SEQ ID NO:10) C-TRPNNNTRKS ITK--GPGRV IYAT-GQIIGD -IRKAH-C (SEQ ID NO:11) C-TRPNNNTRKR ITM--GPGRV YYTTGQIIGD -IRRAH-C (SEQ ID NO:12) C-TRPGSDKRQS TPI--GLGQA LYT-TRGRTKI -IGQAH-C
(SEQ ID NO:13) C-TRPGSDKKIR QSIRIGPGKV FYAKGG---I -TGQAH-C
(SEQ ID NO:14) C-TRPNNNTKKG IAI--GPGRT LYAREKIIGD -IRQAH-C
(SEQ ID NO:15) C-TRPNNHTRKR VTL--GPGRV WYTTGEILGN -IRQAH-C
(SEQ ID NO:16) C-TRPGNNTRRG SHF--GPGQA LYT-TGIVGDI -RRAY-C
(SEQ ID NO:17) C-TRPDNKITSRQ-TPI--GLGQA LYTTRIKGDI -RQAY-C
(SEQ ID NO:18) C-TRPNNNVRRR-HIHI-GPGRA FYTGEIRNI -RQAH-C
(SEQ ID NO:19) C-TRPYKNTRQS-TPI--GLGQA LYT-TRTKSI -GQAH-C
(SEQ ID NO:20) C-TRPNNNTTRS-IHI--GPGRA FYATGDIIGTIRQAH-C
(SEQ ID NO:21) C-TRPNYNKRKR-IHI--GPGRA FYTTKNIIGDIRQAH-C

The production of the amplifying molecules of the invention by using a sequence containing at least one neutralization epitope and particularly one of those from the list above and one carrier sequence having at least one T-epitope, may be achieved by binding these sequences or by physical combination in the same composition.

To be fully effective, priming and amplifying antigens must be enhanced, for example and preferably by lipid adjuvants, such as derivatives of muramyl dipeptide in lipid emulsions, or incomplete Freund's adjuvant.

The priming and amplifying antigens are preferably administered intramuscularly to a host, such as a primate, and especially a human. Following are typical immunization schedules that can be employed for gp160 and peptides of HIV.

| gp160 (months) | Peptides (months) |
|---|---|
| 0, 1, (2), 6 | 12, 13 |
| 0, 1, 2, 12 | 13, 14 |
| 0, 1, 2, 12 | 1, 2, (12) |

It will be understood that these immunization schedules are merely representative and that the schedules can be varied to obtain the optimum response in the host. Similarly, the amounts of the priming and amplifying antigens can be varied. For example, about 150 μg of gp160 in SAF-1™ adjuvant can be administered as indicated, followed by administration of the peptides in amounts of typically 100 μg of each peptide.

Finally, the relative proportions of the peptides involved can vary according to the desired final proportions of each peptide in the final preparation. In particular, these proportions will be adjusted as a function of the immunogenicity of each peptide and the number of functional groups carried by each one, which are capable of entering into the conjugation reaction with complementary functional groups, at least when these peptides are coupled to a carrier molecule.

In a particular application of the invention, the injection of amplifying peptides is replaced by the administration of particles, virus, or bacteria, which are recombinants expressing the neutralization epitope of the virus under consideration on their surface and/or during their multiplication and in this way are capable of inducing neutralizing antibodies against said retrovirus: HBc antigen particles; HBs antigen particles; bacteria expressing the neutralization epitope in surface or cytoplasmic proteins, such as, for example, the lamB receptor; picorna virus chimeras, such as, for example, poliovirus-HIV chimeras; poxvirus recombinants; adenovirus recombinants or adenovirus chimeras, etc. Depending on the live vector selected for the presentation of the neutralization epitope, this administration can be carried out in the form of live vaccine administered orally (for example, chimeras constructed from Sabin poliovirus strains or from human adenoviruses, or from attenuated strains of Salmonella, Shigella, or other enterobacteria, or from any organism, virus, yeast, bacteria, capable of inducing an immune response after oral administration) or in the form of live vaccine administered by the parenteral route (for example, recombinant poxvirus) or even in the form of inactivated vaccine by the parenteral route (for example, chimeras constructed from the Mahoney strain of poliovirus, or inert particles of HBsAg or HBcAg).

In another particular embodiment of the invention, the antigen (envelope glycoprotein), which is injected for the priming of the vaccination, i.e., the envelope glycoprotein of the virus, is presented under the form of particles such ISCOM (Immune Stimulating Complex, comprising an association of an antigenic protein with a glycoside Quil A) or liposomes.

The priming antigen and/or the peptide can be also associated with live recombinant microorganisms, such as viruses or bacteria (for instance the poxvirus or BCG: Bacile de Calmette Guerin) or any live vaccine modified to express the envelope glycoprotein or the peptide derived therefrom.

The envelope glycoprotein and/or the peptide derived therefrom can also be presented by inactivated particles, for instance viral particles, such as the HIV virus or a part of this virus, or particles without genome. Such particles without genome have been described to produce vaccine by Haffar O. et al., Journal of Virology, 64:2653–2659 (1990). These particles can be called HIV-like particles in the case of HIV virus: for the purpose of the invention they do not contain the complete HIV genome, but they enable the exposition at their surface of the virus components of the composition of the invention.

In another embodiment of the invention, the envelope glycoprotein antigen is combined in a mixture with other antigens. For instance, when the priming antigen is the HIV envelope glycoprotein, one or several antigens, such as gag, nef, vif, pol, GPG or GLG antigens, can be combined with it, as they can be combined with the peptides of the composition.

The invention also comprises the compositions above described, wherein the env glycoprotein is replaced by or associated with a fragment thereof. This fragment has advantageously more than 50 amino acids and is characterized in that it has the immunogenic properties of the glycoprotein in the context of the invention.

The invention also concerns monoclonal or polyclonal antibodies, which recognize the glycoprotein and/or peptides of the composition. These antibodies can be associated in a mixture and used, for instance, for serotherapeutic purposes.

EXAMPLE 1

Immunization of a chimpanzee with HIV-1 BRU and the glycoprotein of this isolate; amplification of the response with a BRU env oligopeptide coupled to KLH.

Chimpanzee 339 (FUNFACE) was first immunized with three injections at one month intervals of 250 μg of purified HIV-1 BRU virus, inactivated by treatment with 0.025 percent formalin for 48 hours at 30° C. and 0.025 percent betapropiolactone for 30 minutes at 37° C., combined with Syntex™ adjuvant containing 1 mg/ml threonyl-MDP in an emulsion of 5 percent squalane and 2.5 percent pluronic polymer. These injections were followed by a first booster at 7 months and a second booster one year later.

The animal then received five injections of BRU virus envelope glycoprotein (gp160) purified from supernatant of BHK-21 cell cultures infected with a vaccinia virus recombinant (strain VVenv 1163) having a genome for which genetic recombination techniques were used to insert the sequences of HIV-1 BRU coding for gp160env modified through oligonucleotide site-directed mutagenesis to eliminate the sequences involved in gp120/gp41 cleavage and from which the transmembrane hydrophobic zone was deleted, as described in Kieny et al. in 1988 (Prot. Engineering 2:219–226). The purified protein was used in an amount of 125–150 μg per intramuscular injection in the presence of Syntex™ adjuvant. To prepare the glycoprotein, the culture medium of BHK cells infected with VV-1163 was concentrated by precipitation with ammonium sulfate, then with trichloracetic acid, and the glycoprotein was then purified by three successive runs of affinity chromatography over lentil lectin, ion exchange over cation-exchange resin, and high-performance liquid chromatography (HPLC). The recombinant gp160 obtained in this way is 95 percent pure. It is recognized by monoclonal antibodies specific of the gp160 of HIV-1 and particularly by neutralizing antibodies 110-4 specific for the major neutralization epitope of the BRU isolate. Moreover, it shows a strong affinity for the CD4 receptor of T4 lymphocytes.

The level of antibodies induced in response to injections of inactivated virus (ELISA determination: 1/200,000 with the Diagnostics Pasteur ELAVIA™ kit; neutralizing titer: 1/400 by measurement of 50% inhibition of the formation of immunofluorescence foci; 1/64 by measurement of 90% inhibition of syncytia formation in CEM-SS cells), was not changed appreciably by the injection of gp160.

The animal was given 300 μg of preparation of synthetic peptide having the sequence Y N T R K S I R I Q R G P G R A F V T I G K I G N corresponding to the neutralization epitope of the BRU isolate, the tyrosine residue (Y) being coupled to hemocyanine (KLH) with bis(diazobenzidine) and combined with Syntex™ adjuvant. The injection was repeated once three weeks later, then a second time at 19 weeks.

Figure 2:
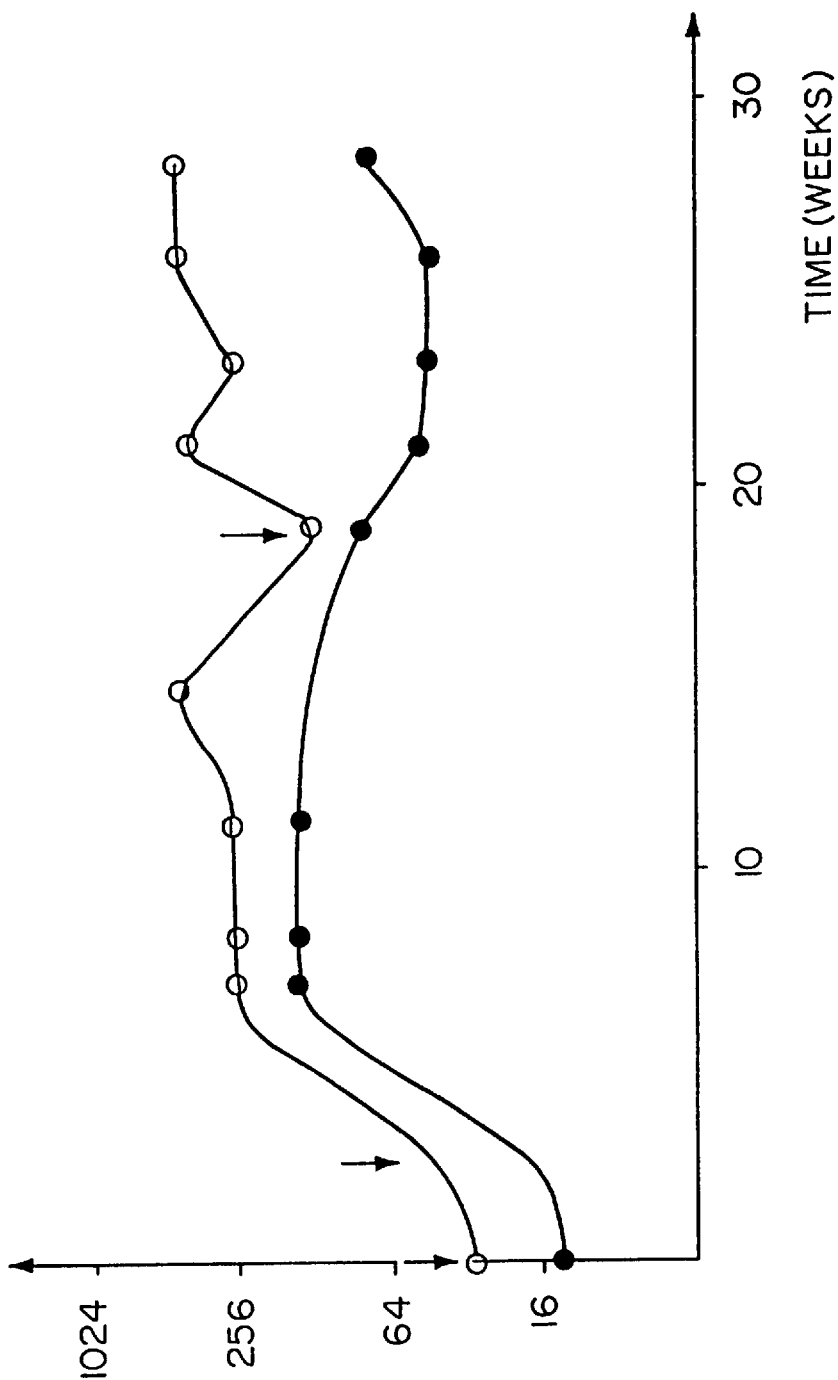

These injections did not result in any increase in antibody titers measured by ELISA (FIG. 1), but they did result in a marked increase in neutralizing antibodies, as can be seen in Table 1 and FIG. 2, as measured by three different antibody titration methods.

TABLE 1

Induction of neutralizing antibodies in the chimpanzee FUNFACE (C-339)

| Date after 1st injection | Level of neutralizing antibodies measured by method | | |
|---|---|---|---|
| (weeks) | A | B | C |
| 0 | 0 | 32 | 100 |
| 3 | 100 | | 150 |
| 8 | 1600 | 128–256 | 800 |

A: 90% inhibition of syncytia in MT4 cells
B: 90% inhibition of syncytia in CEM-SS cells
C: 75% inhibition of immunofluorescence in H9 cells FUNFACE was then challenged at 26 weeks, by administering an intravenous injection of 1 ml of a 1:100 dilution, or 100 TCID50 of a HIV-1 stock titrating $10^4$ TCID50/ml, kindly provided by Larry Arthur (NCI, Frederick). This stock 040 was titered on two occasions in the chimpanzee, which allowed Arthur et al. to determine that its ID50 for the chimpanzees was 4 TCID50. The injection of 40 TCID50 of this stock in unimmunized chimpanzees resulted in the appearance of detectable virus in the lymphocytes of the animal starting two weeks after injection and was followed by anti-HIV seroconversion within four weeks, as observed in the two samples, and as published by Arthur et al. in 1989 (J. Virol., 63: 5046–5053).

The chimpanzee FUNFACE demonstrated apparently total protection against infection with 100 TCID50 of the stock 040 virus, because at up to six months after the challenge injection, no virus was detected in his lymphocytes (as measured either by gene amplification with pol and gag probes, or by coculture with human lymphocytes and assay of reverse transcriptase in 100,000×g pellets obtained from culture supernatants) and at six months, there was no anti-HIV anamnestic response as measured by ELISA or by Western blot (Table 2) and no anti-nef antibody detectable by Western blot.

TABLE 2

Fate of anti-gp160 and anti-major BRU neutralization epitope antibodies after challenge injection of FUNFACE

| | ELISA titer on date indicated | | | | |
|---|---|---|---|---|---|
| Antigen | day of challenge | +1 month | +2 months | +3 months | +4 months |
| gp160 | 179,000 | 127,000 | 89,000 | 44,000 | 18,000 |
| BRU peptide | 6,000 | 3,000 | 2,500 | 1,000 | 1,000 |

EXAMPLE 2

Immunization of a chimpanzee with recombinant antigens env, gag, nef, and vif of HIV-1; amplification of the response by a BRU env oligopeptide coupled to KLH.

Chimpanzee 433 (ROBERT) was first primed with three consecutive scarifications of $2 \times 10^8$ PFU of a recombinant vaccinia virus (VVenv 1139) expressing the gp160env of HIV-1 BRU, then by the intravenous administration of his own lymphocytes which previously had been infected in vitro by the recombinant virus VVenv 1139 and fixed in formaldehyde. The animal then received three consecutive intramuscular injections at one month intervals, then three boosters at 33, 38, and 40 weeks and a last booster at 66 weeks consisting of a mixture of 125–150 μg of each of the following antigens combined with Syntex™ adjuvant: gp160env, purified as described in Example 1 above, and the proteins p18gag, p27nef, and p23vif expressed in *E. coli* and purified as described in French patent application No. 89.11044 of Aug. 18, 1989. Finally, ROBERT received the same BRU peptide coupled to KLH and combined with Syntex™ adjuvant on the same inoculation schedule as FUNFACE did in the previous example.

Figure 3:
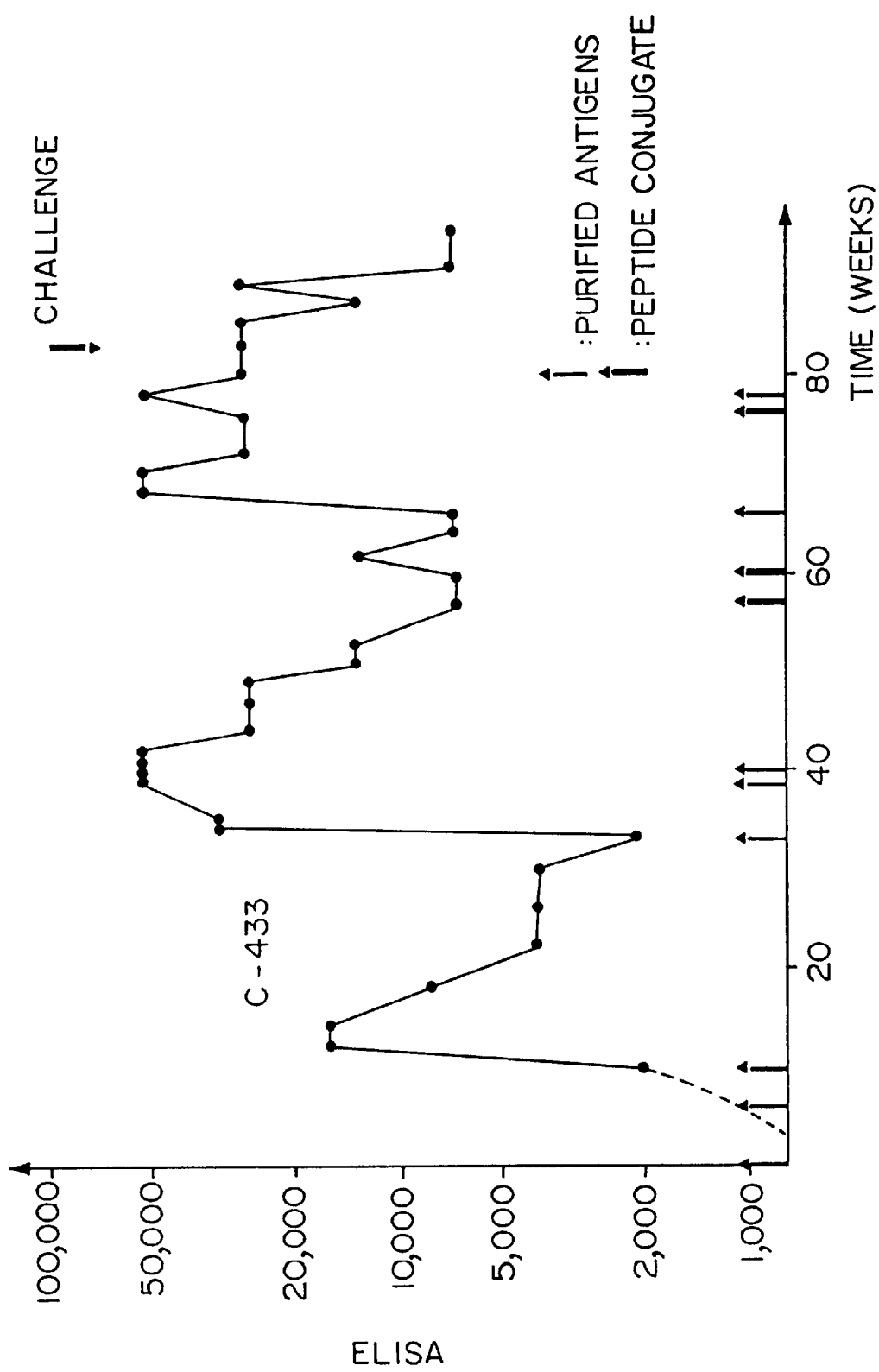

Injections of the peptide-KLH conjugate did not result in any increase in antibody levels as measured by ELISA (FIG. 3), but did result in a marked increase in neutralizing antibodies, as can be seen in FIG. 2 and in Table 3. The neutralizing antibodies were also measured using three different methods:

TABLE 3

Induction of neutralizing antibodies
in the chimpanzee ROBERT (C-433)

| Date after 1st injection (weeks) | Level of neutralizing antibodies measured by method | | |
|---|---|---|---|
| | A | B | C |
| 0 | 200 | 64 | 200 |
| 3 | 200 | | 200 |
| 8 | >800 | 256–512 | >1600 |

A: 90% inhibition of syncytia in MT4 cells
B: 90% inhibition of syncytia in CEM-SS cells
C: 75% inhibition of immunofluorescence in H9 cells Robert was then challenged in parallel with FUNFACE, by the intravenous inoculation of 100 TCID50 of the same stock 040 of HIV-1 virus from NCI as in the previous example. Here again, total protection against infection appears to have been obtained as judging from the absence of virus in the animal's lymphocytes and the negativity of the PCR six months after challenge and by the absence of anti-p25gag and anti-p27nef antibodies, as well as the absence of anamnestic anti-HIV response as measured by ELISA or by Western blot six months after challenge. Table 4 shows the same absence of anamnestic effect on the anti-gp160 and anti-BRU neutralization epitope.

TABLE 4

Fate of anti-gp160 and anti-major BRU neutralization
epitope antibodies after challenge injection of ROBERT

| Antigen | ELISA titer on date indicated | | | | |
|---|---|---|---|---|---|
| | day of challenge | +1 month | +2 months | +3 months | +4 months |
| gp160 | 545,000 | 421,000 | 200,000 | 95,000 | 32,000 |
| BRU peptide | 9,000 | 6,000 | 3,000 | 3,000 | 4,000 |

EXAMPLE 3
Immunization of a chimpanzee with gp160env and p18gag of HIV-1 antigens; amplification with HIV-1 env peptides not coupled to a carrier molecule.

Three chimpanzees were used in this experiment: the chimpanzees JOJOTOO (499), IRA (151) and HENRY II (531).

The first, JOJOTOO, received three injections, at one month intervals, of 120–150 $\mu$g of gp160env and p18gag, purified as described above, and mixed with Syntex™ adjuvant. This first series of injections was followed by three boosters of the same antigen given at weeks 33, 38, and 40, and a final booster at 14 months. These injections resulted in the appearance of a high antibody level detectable by Western blot and by ELISA starting immediately after the first three injections, although the level of neutralizing antibodies was relatively low, as described below.

The second chimpanzee, IRA, was immunized with $10^8$ PFU of each of the four recombinant vaccinia virus stocks expressing, respectively, gp160env, p55gag, p27nef, and p23vif of HIV-1 BRU. These inoculations given by the intradermal route, did not lead to the appearance of any neutralizing antibody, but a barely significant level ($\leq 1:200$) of antibody was detectable by Western blot or by ELISA. Chimpanzee IRA was then rested for two years.

The third chimpanzee, HENRY II, was naive in regard to contact with HIV or SIV antigens before the day of the experiment.

On that day the three animals described above were injected intramuscularly with a cocktail composed of 21 synthetic peptides, corresponding to the 21 sequences of the major neutralization epitope (loop V3) of HIV-1 published in Myers et al. Human Retroviruses and AIDS 1989, Los Alamos, Natl. Lab, in the amount of 50 $\mu$g per peptide, in the presence of Syntex™ adjuvant. Each of the peptides had a cysteine at the N-terminal position and another at the C-terminal, and thus represented the entire V-3 loop of a given isolate (amino acids 296–331 of the BRU isolate and corresponding amino acids according to the alignment of Myers et al. Human Retroviruses and AIDS 1989, Los Alamos, Natl. Lab). The animals were reinjected with the same mixture, respectively, 1 and 2 months after the first injection. This immunization with the mixture of peptides (1.05 mg per injection) was followed in JOJOTOO with a significant anamnestic response directed against the gp160 of the BRU isolate and against its major neutralization epitope, as measured by ELISA and by using purified gp160 BRU or BRU peptide as antigen (Tables 5 and 6).

TABLE 5

Induction of anti-gp160 BRU antibodies in response
to the injection of a cocktail of free peptides
corresponding to 21 sequences of the HIV-1
neutralization epitope (ELISA titer: anti-gp160 BRU)

| | Time | | | |
|---|---|---|---|---|
| Chimpanzee | 1st injection (time 0) | 2nd injection (1 month) | 3rd injection (2 months) | 4th injection (3 months) |
| JOJOTOO (499) | 300,000 | 450,000 | 2,500,000 | 700,000 |
| IRA (151) | Negative | ND | 13,000 | 7,000 |
| HENRY II (531) | Negative | ND | Negative | Negative |

ND: not determined

TABLE 6

Induction of BRU anti-neutralization epitope
antibodies in response to the injection of a
cocktail containing 21 peptides (ELISA anti-BRU titer)

| | Time | | | |
|---|---|---|---|---|
| Chimpanzee | 1st injection (time 0) | 2nd injection (1 month) | 3rd injection (2 months) | 4th injection (3 months) |
| JOJOTOO (499) | 6,000 | 10,000 | 380,000 | 200,000 |
| IRA (151) | Negative | ND | 4,000 | 2,000 |
| HENRY II (531) | Negative | ND | Negative | Negative |

ND: not determined

The titers obtained in IRA remained very low, and they were completely negative in HENRY II. These results clearly illustrate the priming effect on the immune response resulting from pre-immunization with gp160.

The increase in the anti-peptide and anti-gp160 titer in JOJOTOO was, however, not accompanied by a marked increase in the anti-HIV ELISA titer, as can be seen (Table 7) by using a commercial diagnostic kit (ELAVIA™ Diagnostics Pasteur).

TABLE 7

Anti-HIV antibody level as measured by ELAVIA

| | Date | | |
|---|---|---|---|
| Chimpanzee | Time 0 1st injection | 2 months 2nd injection | 5 months 3rd injection |
| JOJOTOO (499) | 1,000,000 | 1,600,000 | 400,000 |
| IRA (151) | Negative | 800 | 100 |
| HENRY II (531) | Negative | 200 | Negative |

Figure 4:
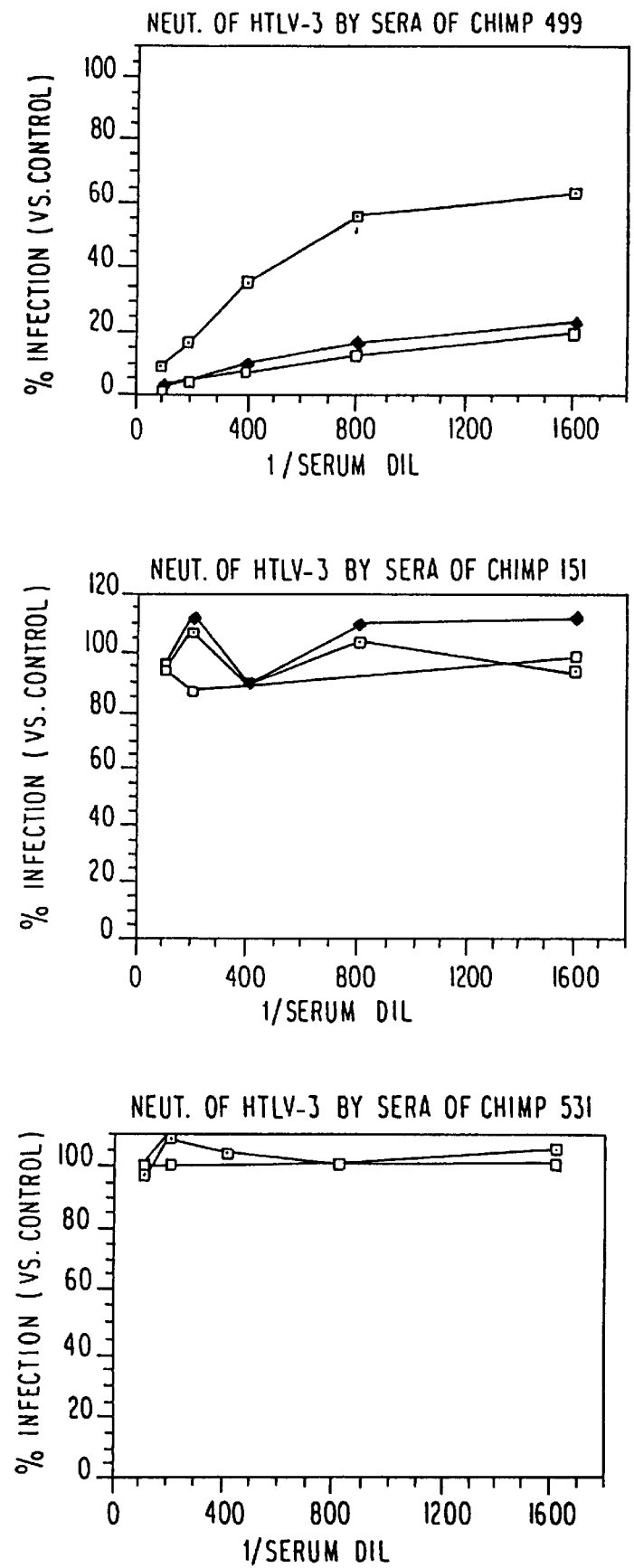

In contrast, the injections of the mixture of synthetic peptides corresponding to neutralization epitopes of the 21 isolates of HIV-1 were followed by a very clear increase in the level of antibodies neutralizing the BRU isolate, as shown in Table 8 and FIG. 4. It is remarkable that this increase was seen only in JOJOTOO, but not in IRA nor in HENRY II, demonstrating the specificity of the priming effect of pre-immunization with gp160 (FIG. 4).

Figure 5:
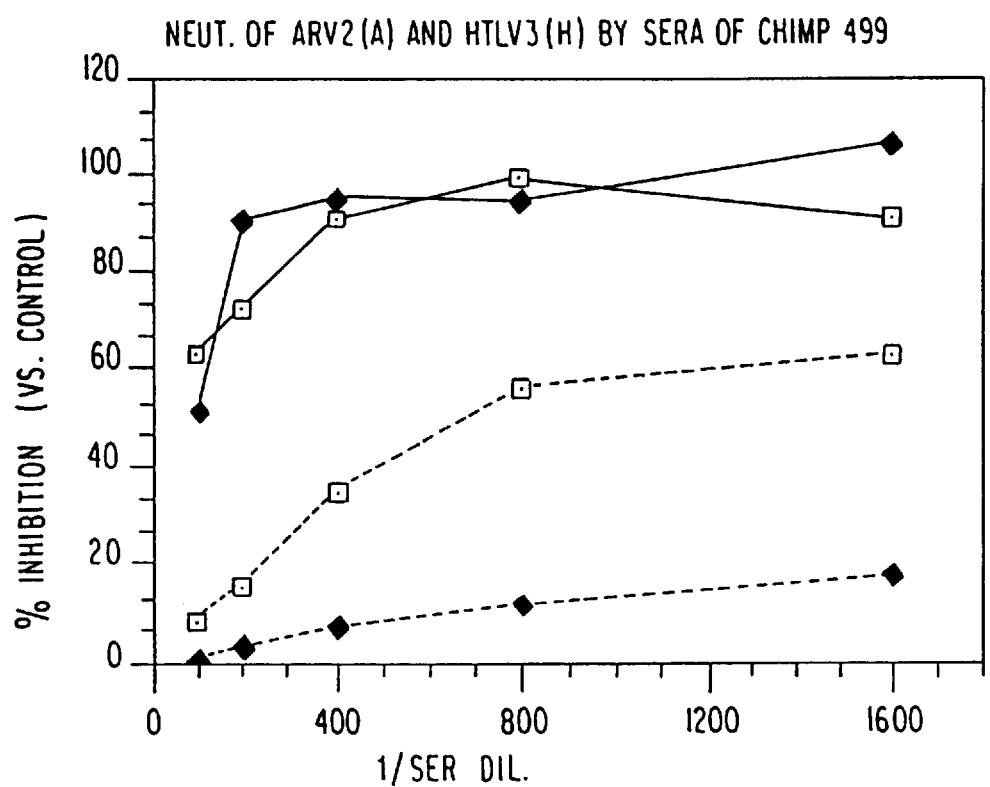

JOJOTOO's neutralizing antibody response is, moreover, specific for the BRU isolate, as can be seen in FIG. 5: his serum does not neutralize the SF2 isolate (ARV-2), but only neutralizes the BRU isolate (HTLV-3=LAV1).

TABLE 8

Level of neutralizing antibodies induced by three injections of a mixture of peptides corresponding to the 21 known sequences of the major neutralization epitope of HIV-1: 75% neutralizing titer measured on CEM-T4 cells (Method C in Table 1).

| Time | |
|---|---|
| 1 month before the first injection | +1 month after the third injection |
| 250 | 2,500 |

Follow-Up Experimental Results

The most stringent test for efficacy of experimental vaccines against the human immunodeficiency virus type 1 (HIV-1) is protection of chimpanzees from infection following live virus challenge. In the study reported here, sustained high titers of neutralizing antibodies were elicited in three chimpanzees after sequential injections of different HIV-$1_{BRU}$ antigen preparations that included whole inactivated virus or purified recombinant proteins, followed by synthetic peptides identical to the major HIV-1 neutralizing epitope, V3. The animals were challenged intravenously with 40 chimpanzee infectious doses (equivalent to 100 50%-tissue culture infectious doses "TCID") of a stock of HIV-$1_{HTLV-IIIB}$. After 6 months of follow-up, all three animals appeared uninfected by serologic and virologic criteria, including PRC analysis and failure to isolate virus from peripheral blood lymphocytes, bone marrow and lymph node tissue. Of two chimpanzees monitored for 1 year, virus was isolated initially from one animal at 32 weeks, but the second and third chimpanzees were virus negative by all assays through 12 months. The third animal has remained virus negative through 7 months of follow-up. These results indicate that it is possible to elicit protection against, or significantly delay infection of, HIV-1 by immunization, thus laying the foundation for development of an HIV-1 vaccine.

Materials and Methods

Animals. Animals used in this study were adult male chimpanzees that had been used previously in hepatitis A, B and non-A and non-B experiments. The chimpanzees were maintained at LEMSIP, New York University Medical Center, in biosafety level 3 facilities. All experimental procedures were done according to institutional guidelines for containment of infectious diseases and for humane care and handling of primates (Moor-Jankowski, J. & Mahoney, C. J. (1989) *J. Med. Primatol.* 18, 1–26).

Immunogens. Sucrose gradient-purified whole HIV was inactivated by incubation with 0.025% beta-propiolactone, followed by 0.025% formalin, and was shown not to contain infectious virus by failure to isolate virus from peripheral blood mononuclear cells (PBMC) of immunized chimpanzees (Girard, M., Kieny, M. P., Gluckman, J. C., Barre-Sinoussi, F., Montagnier, L. & Fultz, P. (1990) in *Vaccines for Sexually Transmitted Diseases* eds. Meheus, A. & Spier, R. (Butterworth Co., Ltd., London), pp. 227–237). Recombinant gp160env was purified from the culture medium of BHK21 cells infected with VV-1163, a recombinant vaccinia virus expressing the gp160env gene modified by site-directed mutagenesis to destroy the gp120/41 cleavage site and to remove the anchor domain of gp41 (Kieny, M. P., Lathe R., Riviere, Y., Dott, K., Schmitt, D., Girard, M., Montagnier, L. & Lecocq. J. P. (1988) *Prot. Engineering* 2, 219–226; and Schmidt, D., Dezutter-Dambuyant, C., Hanau, D., Schmitt, D. A., Kolbe, H. V. J., Kieny, M. P., Cazenave, J. P. & Thivolet, J. (1989) *Comptes Rendus Acad. Sci. Paris*, 308(III), 269–275). Where indicated, the antigen was mixed with recombinant p18gag, p27nef and p23vif antigens that were purified from *E. coli* pTG2153, pTG1166 and pTG1149, respectively, as described (Guy, B., Riviere, Y., Dott, K. Regnault, A. & Kieny, M. P. (1990) *Virology* 176, 413–425; and Kolbe, H. V., Jaeger, F., Lepage, P., Roitsch, C., Lacaud, G., Kieny, M. P., Sabatie, J., Brown, S. W. & Lecocq, J. P. (1989) *J. Chromatography* 476, 99–112). Before each immunization, inactivated whole HIV (250 μg viral protein) or the purified recombinant proteins (125–150 μg each per dose) were mixed with the adjuvant SAF-1™ (Allison, A. C. & Byars, N. E. (1986) *J. Immunol. Methods* 95, 157–168), and 2 ml of the mixtures were injected intramuscularly (IM).

An aliquot (19.8 mg) of a 25-amino acid peptide, with the sequence Y-NTRKSIRIQRGPGRAFVTIGKIGN (Putney, S. D., Matthews, T. J., Robey, W. G., Lynn, D. L., Robert-Guroff, M., Mueller, W. T., Langlois, A. L., Ghrayeb, J., Petteway, S. R. Weinhold, K. J., Fischinger, P. J., Wong-Staal, F., Gallo, R. C. & Bolognesi, D. P. (1986) *Science* 234, 1392–1395; Rusche, J. R., Kavaherian, K., McDanal, C., Petro, J., Lynn, D. L., Grimaila, R., Langlois, A., Gallo, R. C., Arthur, L. O., Fischinger, P. J., Bolognesi, D. P., Putney, S. D. & Matthews, T. J. (1988) *Proc. Natl. Acad. Sci. U.S.A.* 85, 3198–3202; and LaRosa, G. J., Davide, J. P., Weinhold, K., Waterbury, J. A., Profy, A. T., Lewis, J. A., Langlois, A. J., A. J., Dressman, G. R. Boswell, R. N., Shadduck, P., Holley, L. H., Karplus, M., Bolognesi, D. P., Matthews, T. J. Emini, E. A. & Putney, S. D. (1990) *Science* 249 932–935) was treated first with citraconic acid and then was coupled to 19.3 mg keyhole limpet hemocyanin (KLH) by N-terminal tyrosyl linkage using bis-diazobenzidine (pH 9.0). After the block on amino groups was removed, the peptide-KLH conjugate was dialyzed for 24 hours against PBS to remove excess free peptide. After formulation with SAF-1™, immunizations with the V3 peptide-KLH conjugate (300 μg peptide per dose) were done by the IM route.

Challenge Virus. The challenge inoculum was from a stock of HIV-1 strain HTLV-IIIB (obtained from L. Arthur), which had been titrated in chimpanzees and used in other HIV vaccine challenge studies (Arthur, L. O., Bess, J. W., Waters, D. J., Pyle, S. W., Kelliher, J. C., Nara, P. L., Krohn, K., Robey, W. G., Langlois, A. J., Gallo, R. C. & Fischinger, P. J. (1989) *J. Virol.* 63, 5046–5053; and Berman, P. W., Gregory, T. J., Riddle, L., Nakamura, G. R., Champe, M. A., Porter, J. P., Wurm, F. M., Hershberg, R. D., Cobb, E. K. & Eichberg, J. W. (1990) *Nature* (London) 345, 622–625). The infectivity titer of this HIV-1 stock is considered to be $10^4$ $TCID_{50}$ per ml and $4 \times 10^3$ infectious units per ml for chimpanzees. The chimpanzees were challenged IV with 1 ml of a 1:100 dilution. Aliquots of these same 1:100 dilutions were titrated in quadruplicate by twofold serial dilution and infection of $1 \times 10^5$ H9 cells in 96-well microtiter plates. After incubation for 6 days, infection was scored by immunofluorescence assay. By this method, the challenge inoculum had a titer of greater than 64 immunofluorescent focus-forming units (end-point not reached) for the first aliquot and 170 for the second.

Neutralization Assay. Neutralization activity in serum samples from immunized chimpanzees was determined by inhibition of syncytia formation in CEM-SS cells, as described (Nara, P. L., Hatch, W. C., Dunlop, N. M., Robey, W. G., Arthur, L. O., Gonda, M. A. & Fischinger, P. J. (1987) *AIDS Res. Human Retroviruses* 3, 283–302), or inhibition of immunofluorescent foci in H9 cells.

Virus Isolation. PBMC or bone marrow cells (obtained as aspirates) from immunized and challenged chimpanzees were cultured with normal human PBMC, as described (Fultz, P. N., McClure, H. M., Swenson, R. B., McGrath, C. R., Brodie, A., Getchell, J. P., Jensen, F. C., Anderson, D. C., Broderson, J. R. & Francis, D. P. (1986) *J. Virol.*, 58, 116–124). In some experiments, $CD^+4$-enriched lymphocytes were obtained from chimpanzee PBMC by separation with magnetic beads to which were attached monoclonal antibodies specific for the CD8 cell-surface antigen (Dynabeads, Robbins Scientific). The $CD^+4$-enriched cells were stimulated 2 days with concanavalin A (10 μg/ml) before being cultured alone or cocultured with phytohemagglutinin (PHA)-stimulated normal human PBMC in RPMI-1640 medium with 10% fetal bovine serum, glutamine, gentamicin and recombinant interleukin-2 (8 units/ml; Boehringer Mannheim). Lymph node tissue obtained by biopsy was minced with scissors and cultured with human PBMC. All cultures were maintained and monitored for reverse transcriptase activity for 6 weeks before being discarded.

Polymerase Chain Reaction (PCR). Both single- and double-round (nested) PCR were performed periodically with PBMC or lymph node cells from challenged chimpanzees. Single-round PCR was as described (Laure, F., Rouzioux, C., Veber, F., Jacomet, C., Courgnaud, V., Blanche, S., Burgard, M., Griscelli, C. & Brechot, C. (1988) *Lancet* 2, 538–541). Briefly, 2 μg DNA were used with 2 units Taq-1 DNA polymerase for 40 cycles at 94° C., 55° C., and 72° C. (1 min each). Two primer pairs were used: one corresponded to nucleotides 2393–2417 and 2675–2700, encoded by the pol gene, and the other corresponded to nucleotides 5367–5385 and 5694–5711, encoded by the tat gene. To show specificity of the PCR, amplified DNA fragments were hybridized with [$^{32}$P]-labeled internal pol and tat gene probes. The positive control consisted of DNA from the 8E5 cell line persistently infected with LAV-1. For nested PCR, the primers for the first round of PCR, performed as described (Mullis, K. B. & Faloona, F. A. (1987) *Methods Enzymol.* 155, 335–350) were: 5'(SEQ ID NO:22) -GCTTCTAGATAATACAGTAGCAACCCTCTATTG-3', corresponding to a 3-base clamp sequence, an Xba1 restriction site and nucleotides 1025–1048 of the HXB2 genome, and: 5'(SEQ ID NO:23)-GTCGGCCTTAAAGGCCCT-GGGGCTTGTTCCATCTATC-3', corresponding to a 3-base clamp sequence, a Not1 restriction site and nucleotides 5573–5553 of the HXB2 genome. From the first round, 2.5 μl of the product was reamplified with primers SK145 and SK150 (Kwok, S. & Kellogg, D. E. (1990) in *PCR Protocols: A Guide to Methods and Applications*: eds. Innis, M. A., Gelfand, D. H., Sninsky, J. J. & White T. J. (Academic Press, Inc., San Diego, Calif.) pp. 337–347), over a region from nucleotides 1366 to 1507 on the HXB2 genome.

TABLE 9

Immunization regimens of chimpanzees with various HIV-1 antigens

| Animal | Recombinant VV-1139 | Inactivated HIV | Recombinant antigens | | | | V3 peptide |
|---|---|---|---|---|---|---|---|
| | | | gp160 | gag | nef | vif | |
| C-433 | + | + | + | + | + | + | + |
| C-339 | − | + | + | − | − | − | + |
| C-499 | − | − | + | + | − | − | + |

For C-433 and C-339, times of immunizations and virus challenge were calculated from the time that C-433 received its first immunization with VV-1139, which is considered week 0. Chimpanzee C-433 was first immunized with a recombinant vaccinia virus, VV-1139, that expresses a non-cleavable version of the HIV-1$_{BRU}$ gp160env antigen (Kieny, M. P., Lathe R., Riviere, Y., Dott, K., Schmitt, D., Girard, M., Montagnier, L. & Lecocq. J. P. (1988) *Prot. Engineering* 2, 219–226). VV-1139 was administered on weeks 0, 8 and 21 by scarification on the upper back with a two-pronged needle ($2 \times 10^8$ PFU per inoculum). At week 27, PBMC from C-433 were stimulated with PHA, cultured in medium containing IL-2 and then infected with VV-1139 at a multiplicity of infection of 7. Following culture for an additional 16 hours, the PBMC were fixed with 0.8% paraformaldehyde and reinjected into C-433 by the IV route (Zagury, D., Bernard, J., Cheynier, R., Desportes, I., Leonard, R., Fouchard, M., Reveil, B., Ittele, F. D., Lurhama, Z., Mbayo, K., Wane, J., Salaun, J. J., Goussard, B., Dechazal, L., Burny, A., Nara, P. & Gallo, R. C. (1988) *Nature* (London) 322, 728–731). At weeks 48, 54, 58, 81, 86, 88, 114 and 124, C-433 was inoculated IM with mixtures of purified gp160env, p18gag, p27nef and p23vif (125–250 μg each per dose) formulated with SAF-1™.

Chimpanzee C-339 was first immunized on week 33 by IM injection of inactivated HIV (125 μg viral protein) mixed with SAF-1™ (1 mg threonyl muramyl dipeptide), followed by booster inoculations on weeks 37, 41, 62 and 124. C-339 was then inoculated with purified gp160env only (125 μg per dose) on weeks 66, 74, 81, 85 and 87. The V3 peptide (300 μg peptide per dose) was administered IM on weeks 105, 108 and 126.

C-339 and C-433 were challenged on week 131 with 100 $TCID_{50}$ of HIV-1$_{HTLV-IIIB}$. C-449 was inoculated IM with a mixture of gp160env, p18gag and SAF-1™ on weeks 0, 6, 10, 33, 38, 66 and 76. (Note: week 0 for C-499 corresponds to week 48 for C-433 and C-339.) A mixture of 21 free V3 peptides (100 μg each per dose) was administered IM with SAF-1™ on weeks 79, 83, 87 and 102. C-499 and C-087, a naive control, were challenged on week 106 and 100 $TCID_{50}$ of HIV$_{HTLV-IIIB}$.

Results

Figure 6A:
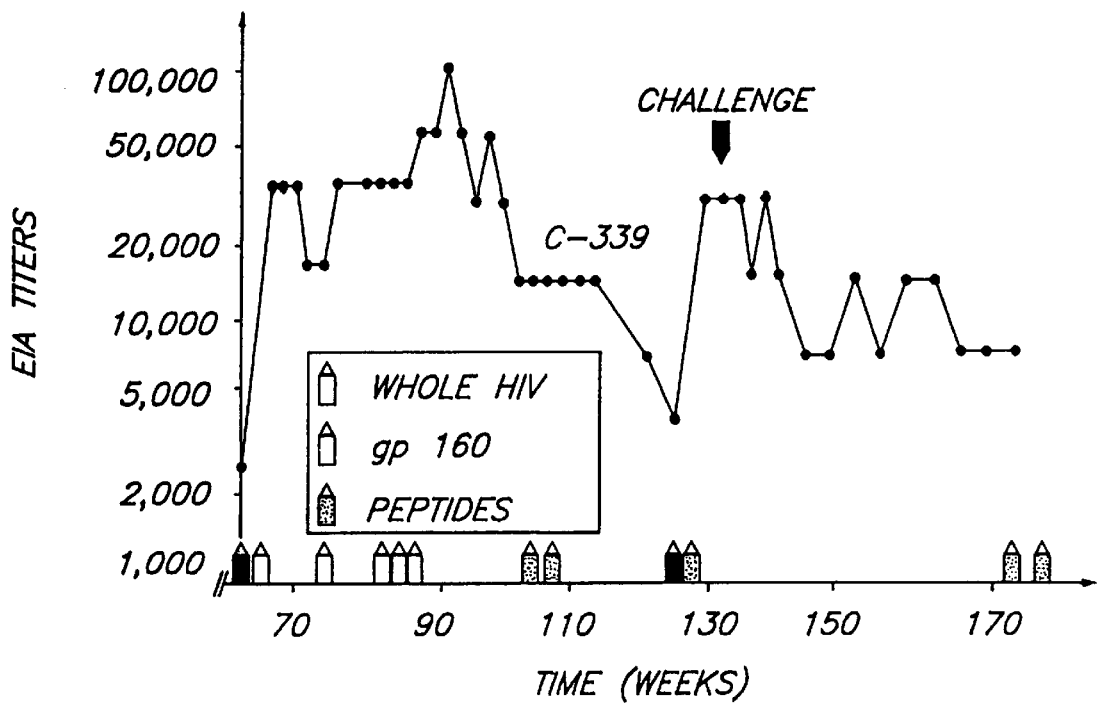

Immunization of chimpanzee C-339 with formalin- and beta-propiolactone-inactivated whole HIV mixed with the adjuvant SAF-1™ resulted in high titers of antibodies to gag- and env-encoded proteins, as measured by enzyme immunoassay (EIA), a low neutralizing antibody response, and no detectable cell-mediated immune response. In an effort to enhance immune responses, C-339 was immunized with purified recombinant gp160env. Following one intradermal inoculation of gp160env with BCG in multiple sites on the chest, C-339 was given four successive IM injections of the same antigen formulated with SAF-1™. Total EIA antibody and neutralizing antibody titers were determined periodically; however, during the course of immunization, both remained unchanged and decreased rapidly after the injections were discontinued (FIG. 6A).

Figure 7:
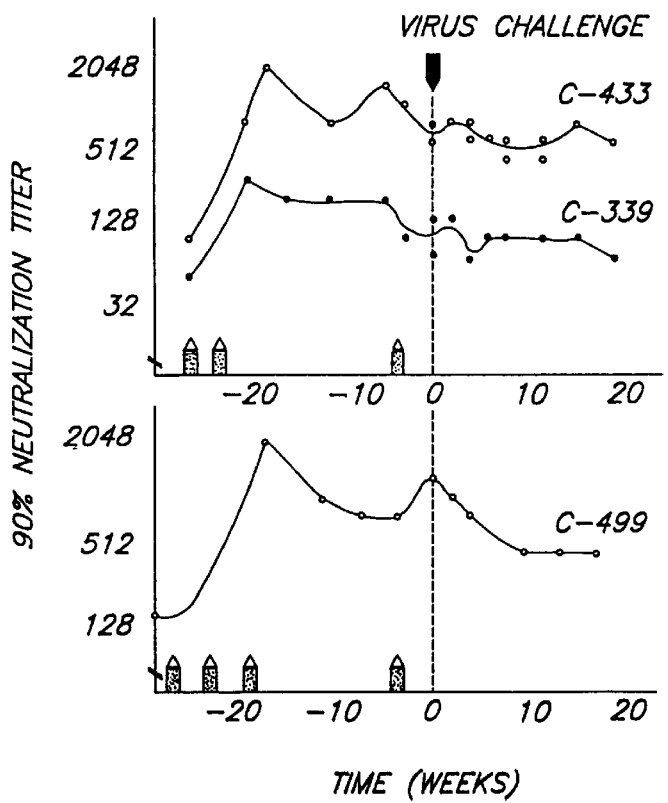

In HIV-infected persons, the majority of HIV-neutralizing antibodies are directed against the third hypervariable region of the external envelope glycoprotein, termed the V3 loop (Putney, S. D., Matthews, T. J., Robey, W. G., Lynn, D. L., Robert-Guroff, M., Mueller, W. T., Langlois, A. L., Ghrayeb, J., Petteway, S. R., Weinhold, K. J., Fischinger, P. J., Wong-Staal, F., Gallo, R. C. & Bolognesi, D. P. (1986) *Science* 234, 1392–1395; Rusche, J. R., Kavaherian, K., McDanal, C., Petro, J., Lynn, D. L., Grimaila, R., Langlois, A., Gallo, R. C., Arthur, L. O., Fischinger, P. J., Bolognesi, D. P., Putney, S. D. & Matthews, T. J. (1988) *Proc. Natl. Acad. Sci. U.S.A.* 85, 3198–3202; and LaRosa, G. J., Davide, J. P., Weinhold, K., Waterbury, J. A., Profy, A. T., Lewis, J. A., Langlois, A. J., A. J., Dressman, G. R. Boswell, R. N., Shadduck, P., Holley, L. H., Karplus, M., Bolognesi, D. P., Matthews, T. J. Emini, E. A. & Putney, S. D. (1990) *Science* 249 932–935). Antibodies to epitopes within the loop abrogate virus infectivity, probably by preventing fusion of the viral envelope to the target cell membrane. Neutralizing antibodies to V3 epitopes can, in fact, be added as long as 40 to 60 minutes after virus binds to the cell and still prevent infection (Nara, P. L., (1989) in *Vaccines* 89, eds. Lerner, R. A., Ginsberg, H., Chanock, R. M. & Brown, F. (Cold Spring Harbor Laboratory, Cold Spring Harbor, N.Y.) pp. 137–144). Therefore, to determine whether immunization with the V3 loop would boost neutralizing antibody titers, C-339 was injected with an oligopeptide of 25 amino acids, having the V3 sequence of HIV-$1_{BRU(IIIB)}$, cross-linked to KLH and formulated with SAF-1™. No change in EIA titer was observed (FIG. 6A), but a significant increase in neutralizing antibody titers, which were sustained for several months, was obtained following the second immunization at week 108 (FIG. 7A).

Figure 6B:
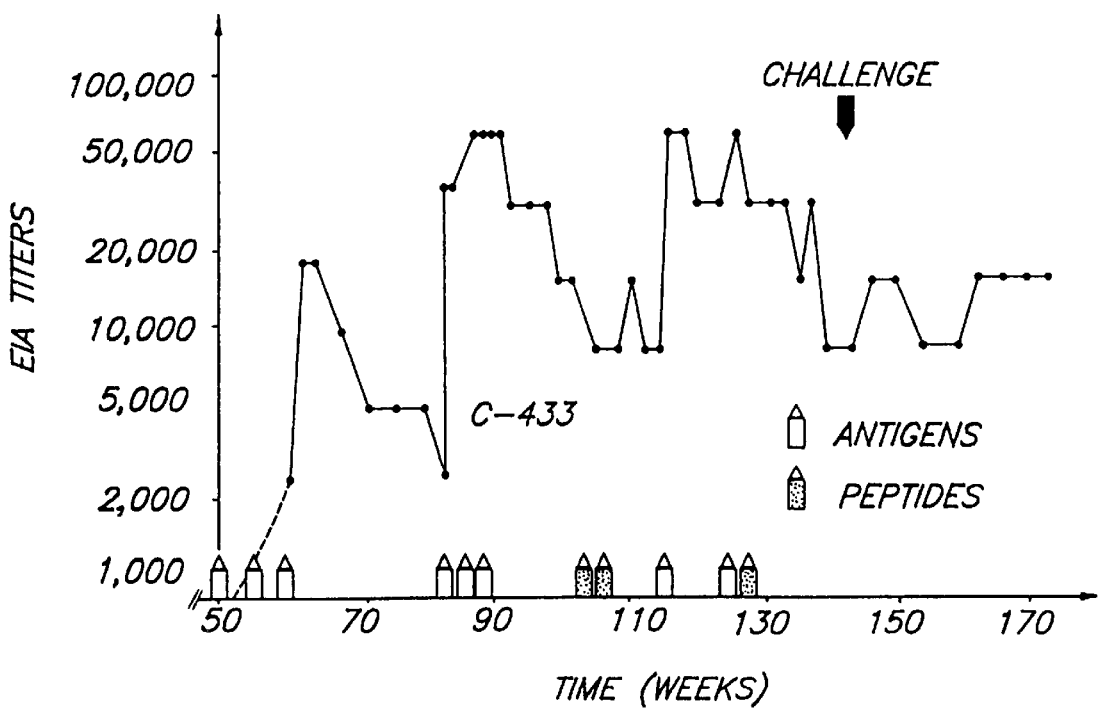
Figure 6C:
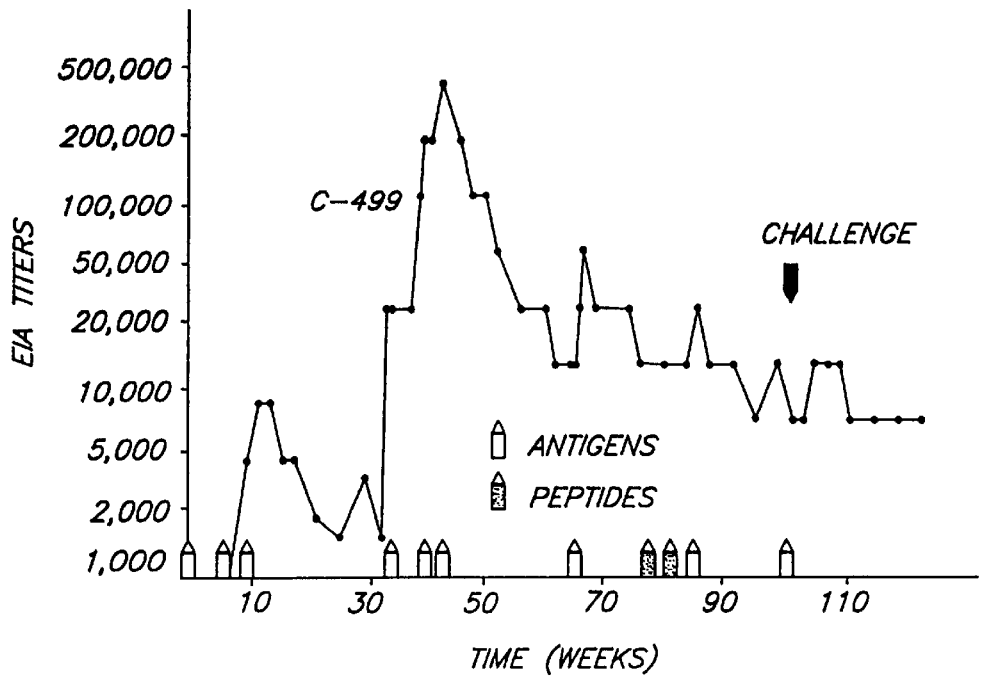

Another chimpanzee, C-433, that had been primed by vaccination with VV-1139 (Kieny, M. P., Lathe R., Riviere, Y., Dott, K., Schmitt, D., Girard, M., Montagnier, L. & Lecocq. J. P. (1988) *Prot. Engineering* 2, 219–226), was immunized repeatedly with 125–250 μg each of recombinant soluble gp160env, p18gag, p27nef and p23vif (Table 1). The anti-HIV antibody response induced by this regimen was clearly transient, with titers rising sharply after each booster injection and then decreasing rapidly (FIG. 6B). The neutralizing antibody and EIA titers of C-433 fluctuated in parallel. Finally, C-433 was injected with the same V3 peptide-KLH conjugate as C-339, according to the same immunization protocol. Neutralizing antibody titers increased significantly after the second injection of the V3-peptide conjugate and remained high thereafter (FIG. 7A); a third immunization 4 months later (week 126) elicited no change in titers.

At the time C-433 first received the purified recombinant proteins (48 weeks), a third chimpanzee, C-499, received an IM injection of purified gp160env and p18gag formulated with SAF-1™. C-499 received six booster innoculations of the same antigens, followed by a series of four injections of a mixture of 21 free (unconjugated) V3 peptides (Myers, G. (1990) in *Human Retroviruses and AIDS*, eds. Myers, G., Josephs, S. F., Wong-Staal, F., Rabson, A. B., Smith, T. F. & Berzofsky, J. A. (Los Alamos National Laboratory, Los Alamos, N.Mex.) in SAF-1. As with C-339 and C-433, C-499's EIA titers declined rapidly after immunization with the purified HIV antigens, and there was no detectable effect of the V3 peptides on EIA titer. There was, however, a significant increase in neutralizing antibody titers (to >2000) following the V3 peptide inoculations (FIG. 7B).

Challenge with Infectious HIV. Because sustained neutralizing antibody titers were achieved, chimpanzees C-433, C-339 and C-499 were challenged by IV inoculation of 100 $TCID_{50}$ (40 chimpanzee infectious doses) of HIV-1. At the time of challenge, 50% neutralization titers by an immunofluorescence inhibition assay were 1:2000, 1:280–350 and 1:2000, and 90% neutralization titers by a syncytia-inhibition assay (Nara, P. L., Hatch, W. C., Dunlop, N. M., Robey, W. G., Arthur, L. O., Gonda, M. A. & Fischinger, P. J. (1987) *AIDS Res. Human Retroviruses* 3, 283–302) were 1:512–1024, 1:128 and 1:1024 for chimpanzees C-433, C-399 and C-499, respectively. Because immunization of C-499 was initiated at a different time from the other two animals, challenge of C-499 occurred 6 months after that of C-399 and C-433, but was done at the same time as that of a naive control animal, C-087. Virus was isolated from C-087's PBMC at 2 weeks post-inoculation (PI) as well as at all subsequent times, showing that a 1:100 dilution of the HIV-1 stock readily infected chimpanzees under our conditions.

Figure 8A:
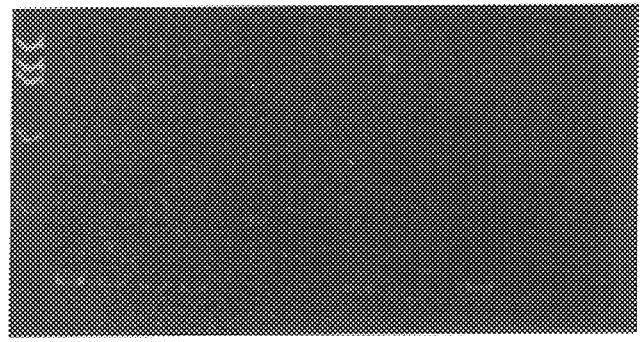
Figure 8B:
Figure 8C:
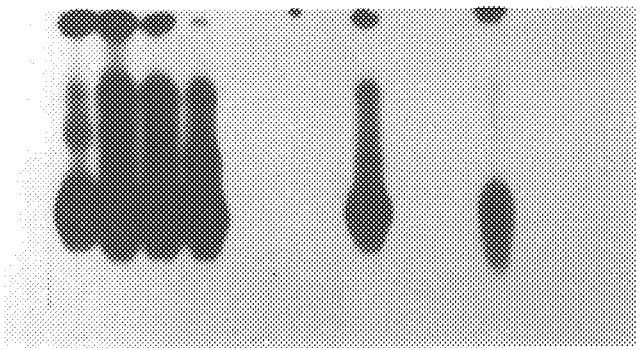

Attempts to Isolate HIV from Immunized and Challenged Chimpanzees. At various times after challenge with HIV-1, three methods were used to assess the infection status of the immunized animals. First, attempts to detect HIV sequences in lymphoid cells by PCR were made periodically (Laure, F., Rouzioux, C., Veber, F., Jacomet, C., Courgnaud, V., Blanche, S., Burgard, M., Griscelli, C. & Brechot, C. (1988) *Lancet* 2, 538–541; Mullis, K. B. & Faloona, F. A. (1987) *Methods Enzymol.* 155, 335–350; and Kwok, S. & Kellogg, D. E. (1990) in *PCR Protocols: A Guide to Methods and Applications*: eds. Innis, M. A., Gelfand, D. H., Sninsky, J. J. & White T. J. (Academic Press, Inc., San Diego, Calif.) pp. 337–347). DNA samples obtained from PBMC of the three chimpanzees at 3 weeks and 3 and 6 months after challenge were tested. Bands with the expected electrophoretic mobility were detected in DNA from a control HIV-infected chimpanzee, but not in PBMC from the vaccinated and challenged animals or from a control naive animal (data not shown). At 6 months after challenge, nested sets of primers were used to perform PCR analysis on DNA from both PBMC and lymph node tissue of the challenged and control chimpanzees (Mullis, K. B. & Faloona, F. A. (1987) *Methods Enzymol.* 155, 335–350). This technique is more sensitive than standard PCR, and in these experiments (repeated at least seven times on all samples), approximately one molecule of viral DNA was found to produce a strong signal when present in $1.5 \times 10^5$ cell-equivalents of DNA. All PBMC and lymph node samples were consistently negative except those from a previously infected chimpanzee, which were always positive (FIG. 8). Thus, at 6 months after challenge, viral DNA was not present in PBMC and lymph node tissues at a frequency greater than one copy per $10^6$ cells.

Second, at weeks 2, 4, 6 and 8, and at monthly intervals thereafter, attempts were made to isolate virus from PBMC by cocultivation of the chimpanzees' PBMC with lymphocytes obtained from normal humans (Fultz, P. N., McClure, H. M., Swenson, R. B., McGrath, C. R., Brodie, A., Getchell, J. P., Jensen, F. C., Anderson, D. C., Broderson, J.

R. & Francis, D. P. (1986) *J. Virol.*, 58, 116–124). Because CD8$^+$ cells have been shown to suppress virus replication not only in HIV-infected humans (Walker, C. M., Moody, D. J., Stites, D. P. & Levy, J. A. (1986) *Science* 234, 1563–1566; and Tsubota, H., Lord, C. I., Watkins, D. I., Morimoto, C. & Letvin, N. L. (1989) *J. Exp. Med.* 169, 1421–1434) and chimpanzees (P.N.F., unpublished data), but also in SIV-infected macaques (Tsubota, H., Lord, C. I., Watkins, D. I., Morimoto, C. & Letvin, N. L. (1989) *J. Exp. Med.* 169, 1421–1434), in some experiments chimpanzee PBMC were depleted of CD8$^+$ lymphocytes before cultures were established. In contrast to virus recovery from the control animal, C-087, virus was not recovered from either total PBMC or CD4$^+$-enriched cells from C-339, C-433, or C-499 at any time during the first 6 months of follow-up. At 6 months PI, inguinal lymph node biopsies were performed on all animals as well as on uninfected and HIV-infected control chimpanzees. Upon cocultivation with normal human PBMC, virus was recovered from the lymph node of the infected control, but not from those of the immunized and challenged chimpanzees (data not shown). Despite the fact that all attempts to detect virus during the first 6 months after challenge had failed, virus was isolated from C-433 by cocultivation of PBMC obtained at 32 weeks and thereafter and of bone marrow obtained 37 weeks after challenge.

Figure 9:
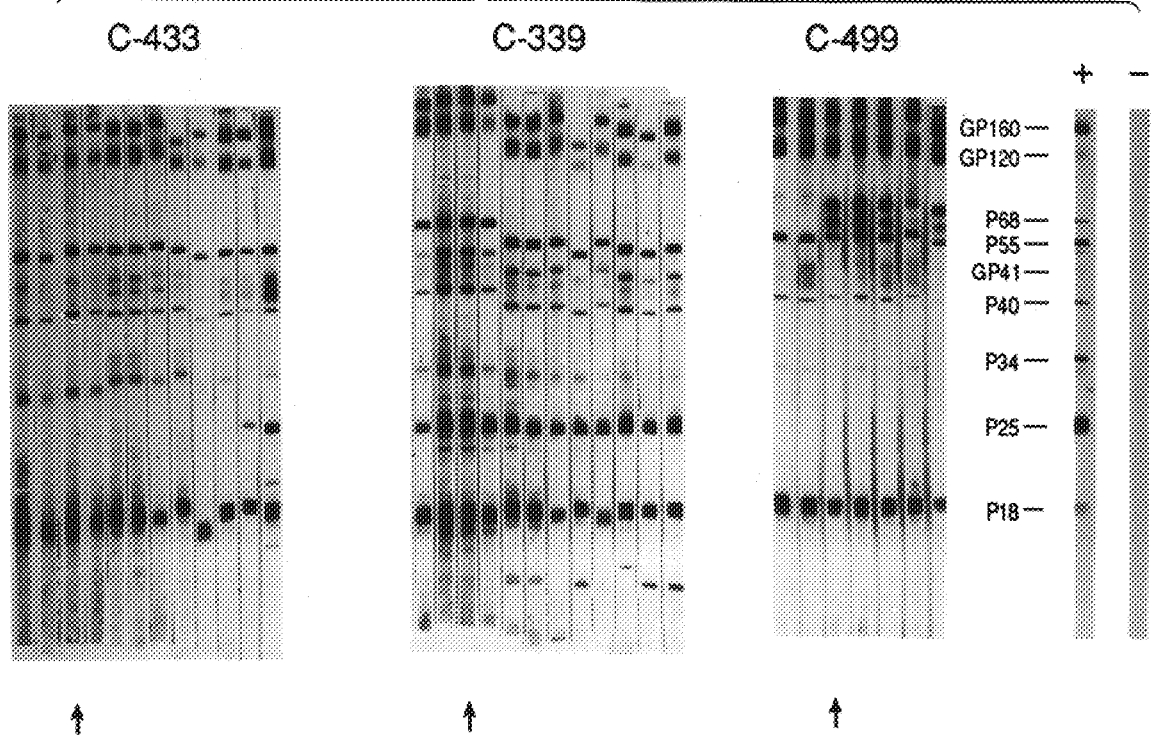

Lastly, the challenged animals were monitored for possible seroconversion to HIV antigens that were not included in their immunization regimens. Immunoblot analysis (Diagnostic Pasteur) showed that C-433 and C-499, which had been immunized with, among other antigens, p18gag but not p25gag, did not seroconvert to p25 during 7 months follow-up; however, at 32 weeks (7½ months) PI, a faint p25 band was observed on immunoblots for C-433, which increased in intensity with succeeding serum samples (FIG. 9). For C-339, which had been immunized with whole inactivated HIV, there were no detectable increases in EIA antibody titers or in apparent levels of antibodies to any HIV-specific proteins (FIG. 9). Also, using purified antigens in immunoblot assays, no antibodies to the vif or nef proteins were detected in serum from C-339 during 12 months follow-up.

The results presented here, as well as those reported by Berman and colleagues (Berman, P. W., Gregory, T. J., Riddle, L., Nakamura, G. R., Champe, M. A., Porter, J. P., Wurm, F. M., Hershberg, R. D., Cobb, E. K. & Eichberg, J. W. (1990) *Nature* (London) 345, 622–625), clearly show that it is possible to elicit a protective immune response in chimpanzees with various HIV-1 antigens. It has been shown that C-499 was protected against establishment of HIV infection, at least through 7 months follow-up, that C-339 was protected for 1 year, and that C-433 was protected partially, as evidenced by the 7-month delay in appearance of virus. It is possible, however, that C-433 also might have been fully protected if the challenge dose had been the same as that used by others (Berman, P. W., Gregory, T. J., Riddle, L., Nakamura, G. R., Champe, M. A., Porter, J. P., Wurm, F. M., Hershberg, R. D., Cobb, E. K. & Eichberg, J. W. (1990) *Nature* (London) 345, 622–625), which was fourfold lower than the dose used herein. Protection was demonstrated by: (1) failure to recover virus from PBMC during monthly attempts and from lymph node tissue at 6 months PI: (ii) negative hybridization signals in PCR analysis of DNA from PBMC at various intervals and from lymph nodes at 6 months PI, and (iii) the absence of antibody responses that normally follow a primary HIV infection or that are characteristic of anamnestic responses in previously vaccinated and challenged animals (Berman, P. W., Groopman, J. E., Gregory, T., Clapham, P. R., Weiss, R. A., Ferriani, R. Riddle, L., Shimasaki, C., Lucas, C., Lasky, L. A. & Eichberg, J. W. (1988) *Proc. Natl. Acad. Sci. U.S.A.* 85 5200–5204; Arthur, L. O., Bess, J. W., Waters, D. J., Pyle, S. W., Kelliher, J. C., Nara, P. L., Krohn, K., Robey, W. G., Langlois, A. J., Gallo, R. C. & Fischinger, P. J. (1989) *J. Virol.* 63, 5046–5053; Girard, M., Kieny, M. P., Gluckman, J. C., Barre-Sinoussi, F., Montagnier, L. & Fultz, P. (1990) in *Vaccines for Sexually Transmitted Diseases* eds. Meheus, A. & Spier, R. (Butterworth Co., Ltd., London), pp. 227–237).

That C-433 appeared to be protected for 7 months, but actually was infected from time of challenge, despite repeatedly negative results for virus isolation and detection by PCR, is worrisome and underscores the fact that HIV can be sequestered such that it defies detection by both virologic and serologic criteria. A similar occurrence was reported (Desrosiers, R. C., Wyand, M. S., Kodama, T., Ringler, D. J., Arthur, L. O., Sehgal, P. K., Letvin, N. L., King, N. W. & Daniel, M. D. (1989) *Proc. Natl. Acad. Sci. U.S.A.* 86 86, 6353–6357) for a macaque immunized with inactivated whole virus and then challenged with infectious SIV. In that study, virus was not recovered initially until 32 weeks and an anamnestic response was not observed until 39 weeks after challenge. The observation in natural HIV infections that persons remained seronegative by conventional tests for extended times, but HIV was detected by PCR or virus isolation (Ranki, A., Valle, S. L., Krohn, M., Antonen, J., Allain, J. P., Leuther, M., Franchini, G. & Krohn, K. (1987) *Lancet* 2, 589–593; and Jehuda-Cohen, T., Slade, B. A., Powell, J. D., Villinger, F., De, B., Folks, T. M., McClure, H. M., Sell, K. W. & Ahmed-Ansari, A. (1990) *Proc. Natl. Acad. Sci. U.S.A.* 87, 3972–3976), suggests that high-risk individuals, such as sexual partners of HIV-infected persons, possibly could be infected despite negative serologic, virologic or PCR analyses.

In view of the complex regimen of immunization undergone by the three chimpanzees, it is difficult to determine which of the many antigens and/or antigen formulations were instrumental in eliciting partial protection. C-339 was immunized successively with inactivated HIV, purified gp160, and the V3 peptide-KLH conjugate. C-433 was immunized first with a vaccinia virus-gp160env recombinant, then with a mixture of purified env, p18gag, nef and vif antigens, and finally with the V3 peptide-KLH conjugate. The simplest immunization regimen was that of C-499; it consisted of purified gp160env and p18gag followed by unconjugated V3 peptides. The antigens that were common to the three animals were gp160env, p18gag and the V3 peptide, but their relative importance remains to be determined. Adequate protection might require multiple antigenic determinants found on more than one viral protein, and/or multiple presentations of the same antigenic determinant.

It is of interest that previously tested prototype vaccines (Berman, P. W., Groopman, J. E., Gregory, T., Clapham, P. R., Weiss, R. A., Ferriani, R. Riddle, L., Shimasaki, C., Lucas, C., Lasky, L. A. & Eichberg, J. W. (1988) *Proc. Natl. Acad. Sci. U.S.A.* 85 5200–5204; Arthur, L. O., Bess, J. W., Waters, D. J., Pyle, S. W., Kelliher, J. C., Nara, P. L., Krohn, K., Robey, W. G., Langlois, A. J., Gallo, R. C. & Fischinger, P. J. (1989) *J. Virol.* 63,5046–5053; Girard, M., Kieny, M. P., Gluckman, J. C., Barre-Sinoussi, F., Montagnier, L. & Fultz, P. (1990) in *Vaccines for Sexually Transmitted Diseases* eds. Meheus, A. & Spier, R. (Butterworth Co., Ltd., London), pp. 227–237; and Hu, S. L. Fultz, P. N., McClure, H. M., Eichberg, J. W., Thomas, E. K., Zarling, J., Singhal, M. C., Kosowski, S. G., Swenson, R. B., Anderson, D., C. & Todaro, G. (1987) *Nature* (London) 328, 721–723) that did not elicit significant titers of neutralizing antibodies in chimpanzees were not effective in preventing experimental infection of the animals. The observation that sustained neutralizing antibody titers were reached in C-339 and C-433 after two injections of the V3 peptide-KLH conjugate and in C-499 after three injections of V3 peptides (FIG. 7), suggests that V3 might be seen differently by the chimpanzee immune system when presented as a peptide than when presented as part of the gp160/120env molecule. We have found by immunoaffinity chromatography that virtually all HIV-neutralizing activity in the serum of the protected chimpanzees could be adsorbed by the V3 peptide (unpublished data of A.P.). The booster inoculations of the V3 peptide(s) might explain why immunization with gp160 resulted in protection of chimpanzees in the subject experiments, but not in those reported by Berman et al. (Berman, P. W., Gregory, T. J., Riddle, L., Nakamura, G. R., Champe, M. A., Porter, J. P., Wurm, F. M., Hershberg, R. D., Cobb, E. K. & Eichberg, J. W. (1990) *Nature* (London) 345, 622–625). In this latter study, two chimpanzees were protected after immunization with gp120, and these animals had three- to four-fold higher titers to the principal neutralizing determinant (PND) found in the V3 loop than the two animals not protected from infection.

The question of whether the protection observed in the present experiment was due solely to neutralizing antibodies or whether other immune mechanisms were involved remains unanswered. At time of challenge, antibody-dependent cellular cytotoxic activity was detected in the serum of C-339, but not in that of the other two chimpanzees. HIV-specific proliferative responses to the soluble proteins p18gag, gp160env, and p27nef (Bahraoui, E., Yagello, M., Billaud, J. N., Sabatier, J. M., Guy, B., Muchmore, E., Girard, M. & Gluckman, J. C. (1990) *AIDS Res. Human Retroviruses* 6, 1087–1088; and Van Eendenburg, J. P., Yagello, M., Girard, M., Kieny, M. P., Lecocq, J. P., Muchmore, E., Fultz, P. N., Riviere, Y., Montagnier, L. & Gluckman, J. C. (1989) *AIDS Res. Human Retroviruses* 5, 41–50) were detected in PBMC from C-433 both before and after virus challenge, but not in PBMC from C-339. Interestingly, after immunization with the V3-KLH conjugate, C-433 displayed a sustained, strong T-helper cell reactivity to the V3 peptide, while C-339 had only a weak response. The responses of C-449 are currently under study. Repeated attempts to detect cytotoxic T lymphocytes (CTL) in PBMC of the vaccinated chimpanzees before, on the day of, and after challenge have failed. It appears, therefore, that the observed protection did not correlate with the T-helper cell or CTL activity.

The results presented here indicate that HIV vaccines can induce protection against virus infection. The high neutralizing antibody response induced by the V3 peptide was type specific; serum from the vaccinated animals at time of challenge neutralized the more diverse HIV-1 isolates RF and MN only marginally (unpublished data). Therefore, it will be necessary to design a vaccine that will induce high titers of neutralizing antibodies to the many HIV variants, but the recent identification (LaRosa, G. J., Davide, J. P., Weinhold, K., Waterbury, J. A., Profy, A. T., Lewis, J. A., Langlois, A. J., A. J., Dressman, G. R. Boswell, R. N., Shadduck, P., Holley, L. H., Karplus, M., Bolognesi, D. P., Matthews, T. J. Emini, E. A. & Putney, S. D. (1990) *Science* 249 932–935) of PND sequences with which a majority of sera from HIV-infected persons react may make this less formidable than previously thought. The apparent success in protecting two chimpanzees and suppression of virus for an extended period in a third animal justify further efforts to develop an HIV vaccine, with the expectation that it will provide long-lasting protective immunity in humans.

Further studies were conducted to ascertain the validity of the dual immunization procedure (priming with gp160 followed by boosting with synthetic peptides with the sequence of the V3 loop of gp120); to compare 3 adjuvants: $Al(OH)_3$, the Syntex adjuvant, SAF-1™, and incomplete Freund adjuvant (IFA); and to test an accelerated schedule of immunization: gp160 at 0 and 1 month, the V3 peptide at 3 and 4 months, and both gp160 and V3 as a last boost at 6 months.

The experiment was carried out in Rhesus macaques (4 animals per lot) using 100 µg of gp160 BRU for priming and a mixture of 200 µg each of V3-BRU (gp120 amino acid residues 302–335) and V3-MN (same residues) for boosting. The animals were bled at monthly intervals and anti-V3 and anti-gp160 antibody (Ab) titers were determined by ELISA. Neutralizing Ab titers were determined by the inhibition of immunofluorescent foci formation assay.

Figure 10:
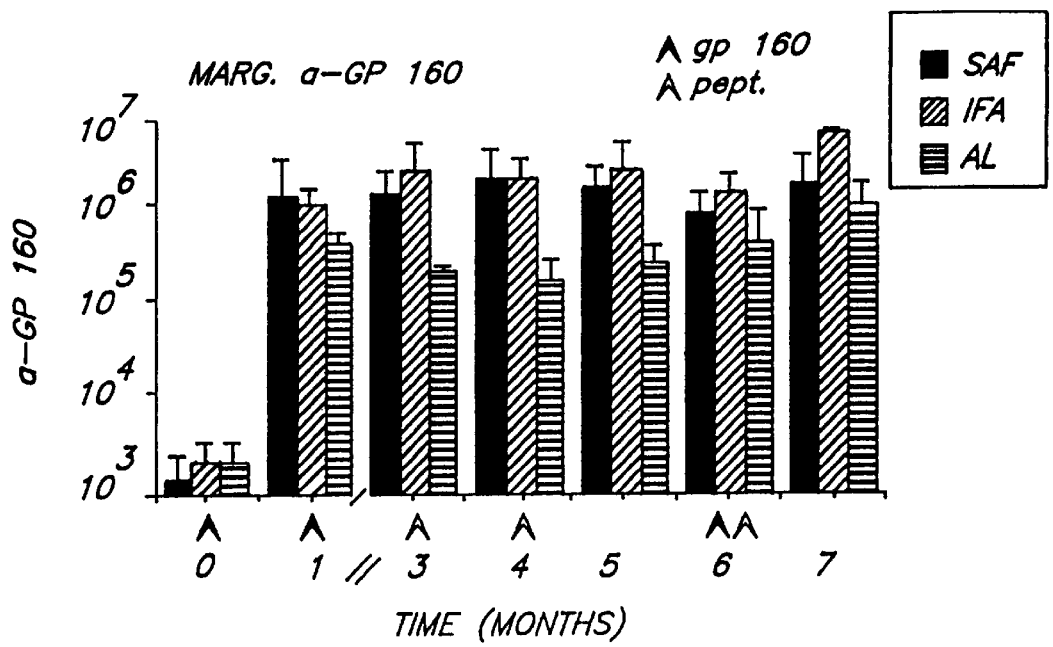

Anti-gp160 Ab were measured by ELISA using plates coated with purified gp160 BRU. A fast anti-gp160 Ab response was observed in the 3 groups of animals (FIG. 10), but the response to the antigen in the groups with IFA and SAF-1™ was from 5 to 10 fold higher than that in the group with alum. Injection of V3 peptides had no effect on anti-gp160 titers. Titers were boosted several fold upon recall injection of gp160 at 6 months, but again, the group with alum had a 2–8 fold lower response than the other 2.

Figure 11:
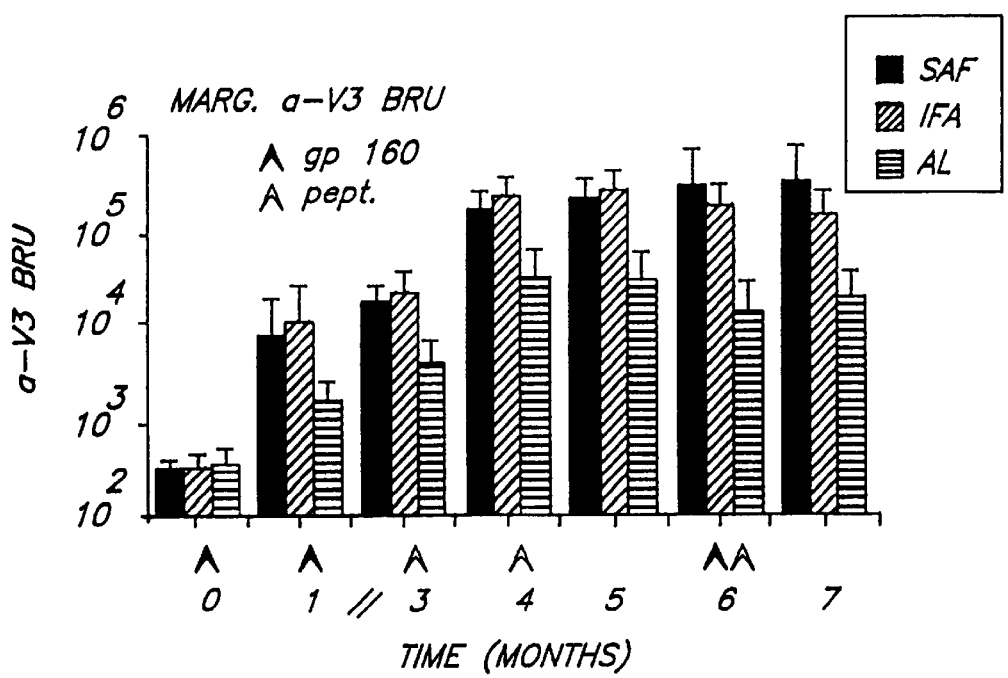

Anti-V3 Ab were measured by ELISA using plaques coated with the BRU peptide. The response to V3 was clearly biphasic in all groups, with a strong booster effect seen upon injection of the V3 peptide at 3 months (FIG. 11). Thus, anti-V3 titers increased 10 fold between months 3 and 4 and then plateaued, confirming the remarkable booster effect of a V3 peptide injection in gp160-primed animals. This was observed irrespective of the adjuvant used in the experiment.

The initial response to V3, measured at month 3, was, however, 5–6 fold higher in the SAF-1™ and IFA groups than in the group with alum. The final anti-V3 titers were altogether about 10 fold higher in the former 2 groups than in the latter. A two-step immunization schedule can be defined as follows:

priming: gp160 at 0 and 1 month
boosting: V3 peptides at 3 months
second boosting: gp160+V3 peptides at 6 months.

The second boost can be placed at a later time, such as 12 months, to increase further the anamnestic response. All pre-immune sera were negative for neutralizing Ab. Titers of neutralizing Ab measured at one month after the second boost (month 7) were the following:

| | Adjuvant | | |
|---|---|---|---|
| Monkeys | $Al(OH)_3$ | SAF-1™ | IFA |
| 1 | 60 | 140 | >450 |
| 2 | neg | 135 | 340 |
| 3 | 123 | >450 | 292 |
| 4 | neg | >450 | 440 |

Here again, there was a definite advantage in using SAF-1™ or incomplete Freund adjuvant over using alum, although the realtive difference in titers was somewhat less pronounced between the various groups.

In conclusion, a fast 2-step anti-HIV immunization schedule for primates is able to induce high anti-V3, high anti-gp160, and high neutralizing Ab responses. This schedule includes:

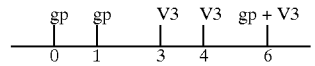

An alternative to that schedule could be:

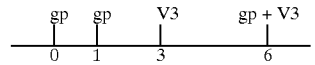

There is an advantage in using the SAF-1™ or incomplete Freund adjuvant rather than Alum [Al(OH)$_3$], as final Ab titers are from 5 to 15 fold higher with the former 2 adjuvants as compared to the latter.

VACCINE PROTECTION OF CHIMPANZEES AGAINST CHALLENGE WITH HIV-1-INFECTED PERIPHERAL BLOOD MONONUCLEAR CELLS

Recent studies have demonstrated that, irrespective of stage of infection or disease, blood of persons infected with the human immunodeficiency virus (HIV) contains both virus-infected cells (also called cell-associated virus) and cell-free virus ( ). These findings imply that transmission of HIV may occur with either or both forms of virus. Although data regarding the quantity and primary form of HIV in vaginal and seminal fluids are limited ( ), it probably can be assumed that both cell-free and cell-associated virus are also transmitted through sexual contact. Therefore, any effective vaccine against HIV must protect against both forms of virus as well as from transmission via mucosal surfaces (sexual) and intravenously (through exchange of blood).

Animal model systems employing either HIV-1 infection of chimpanzees or infection of various macaque species with HIV-2 or the simian immunodeficiency virus (SIV) have been used to demonstrate that vaccination can elicit immune responses capable of protecting against infection with these viruses ( ). However, in all cases, protection was demonstrated only against challenge with relatively low doses of infectious cell-free virus. In the present study we determined (i) whether serum and/or peripheral blood mononuclear cells (PBMC) from HIV-immunized chimpanzees could prevent transmission of cell-associated HIV-1 in vitro, and (ii) whether chimpanzees previously immunized with various HIV-1 antigen preparations would be protected against intravenous challenge with PBMC from an HIV-infected chimpanzee.

As reported previously ( ), chimpanzee C-339 was immunized with various HIV-1 antigens and was subsequently challenged with an intravenous injection of 100 TCID$_{50}$ of cell-free HIV-1. This animal had remained virus negative by multiple criteria and did not develop an anamnestic antibody response to the virus through 40 weeks after challenge. Because unrelated in vivo studies had indicated that immune stimulation induced Increases in HIV-1 expression in long-term infected chimpanzees ( ), and to insure that C-339 had indeed been protected from infection, we attempted to reactivate or induce detectable expression of putative latent virus by stimulating the animal's immune system. At week 40 after challenge, C-339 was inoculated with the Syntex adjuvant formulation, SAF-1™, and at weeks 44 and 48, the animal was injected with a mixture of HIV-1 antigens (inactivated HIV-1$_{LAV-1}$; recombinant antigens gp160env, p25- and p18-gag, and peptides representing the V3 immunodominant loop, all formulated with SAF-1). While none of these inoculations resulted in detection of virus by cocultivation of C-339's PBMC with normal human PBMC, the last two injections of HIV-1 antigen did serve as booster immunizations; increases in total anti-HIV-1 (FIG. 1) and neutralizing (data not shown) antibody titers were observed.

To obtain an indication as to whether C-339's level of HIV-specific immunity might be sufficient to prevent infection by HIV-infected cells, in vitro assays for both humoral and cell-mediated inhibition of transmission were performed. We first tested whether serum from chimpanzee C-339 could prevent transmission of infectious virus from PBMC from an HIV-1-infected chimpanzee to PHA-stimulated normal human PBMC. As a positive control, serum (from an HIV-1-infected chimpanzee) that completely inhibited cell-to-cell transmission (P.N.F., manuscript in preparation) was included in each assay. Compared to serum obtained from C-339 prior to immunization, which had no inhibitory activity, serum from weeks 0 (at time of challenge with cell-free virus) and 52 inhibited virus transmission and production by 68% and 75%, respectively, whereas serum from week 24 inhibited virus production by only 33% (FIG. 2A). The week 24 value is probably a reflection of gradual loss of inhibitory activity after the initial virus challenge, and that at week 52, of an increase in Inhibitory activity due to the two HIV-1 booster injections given to C-339 at weeks 44 and 48.

Second, we tested whether PBMC from C-339, when used as indicator cells, would prevent transmission and replication of virus when cocultivated with PBMC from an HIV-1-infected chimpanzee (C-087). PBMC from C-339 were added at a fixed concentration (2–3×10$^6$ cells/well) to wells of 12-well tissue culture plates. C-087's PBMC were serially diluted 1:4, and cells from each dilution were added to duplicate wells containing PBMC from C-339 (or normal human or chimpanzee PBMC, as controls), starting with a ratio of 1:1. Culture supernatants were monitored periodically for virus production by reverse transcriptase assay. Inhibitory activity was considered to be present in cells from the immunized animals if (i) a larger number of C-087's PBMC were required to yield virus-positive cultures within 6 weeks of observation, and (ii) there was a delay in time at which cultures became virus positive, compared with those cocultures established with PBMC from HIV-1-naive individuals. These assays indicated that C-339 had substantial inhibitory activity on week 40, which was before the two booster injections of HIV-1 antigens (FIG. 2B). Although this inhibitory activity had declined by week 73, enrichment for CD8$^+$ cells by magnetic bead depletion of CD4$^+$ cells resulted in complete inhibition of virus recovery (FIG. 2C). The apparent enhancement of infection with the CD4$^+$-enriched population of C-339's PBMC probably is a function of the greatly increased number of cells capable of supporting replication of HIV-1.

Because the in vitro assays indicated that both serum and PBMC from C-339 had at least some ability to prevent cell-to-cell transmission of HIV-1, C-339 and a negative control chimpanzee, C-435, were challenged intravenously with HIV-1-infected PBMC. The challenge inoculum consisted of cryopreserved PBMC that were obtained from heparinized blood of a chimpanzee, C-087, that had been infected 14 weeks earlier with HIV-1$_{HTLV-IIIB}$ (as a positive control in another vaccine study [ ]). A challenge inoculum consisting of PBMC from an HIV-1-infected chimpanzee was believed to most nearly approximate transmission that occurrs between, for example, intravenous drug users. Since the minimal infectious dose of HIV-infected cells required for infection of chimpanzees had not been determined, and because of the limited number of available chimpanzees, the dose of the challenge inoculum was selected empirically. This selection was based on the results of in vitro titrations of aliquots of the cryopreserved PBMC from chimpanzee C-087, using PHA-stimulated normal PBMC from both humans and chimpanzees as indicator cells ( ). From these assays, it was determined that there was an average of 382 infectious cells per $10^7$ total PBMC in this cryopreserved stock. The two chimpanzees, C-339 and C-435, were inoculated intravenously with a volume of 1 ml, which contained $5.8 \times 10^5$ PBMC or 22 infectious PBMC. This number is a minimum estimate and is based on the assumption that one infected cell is sufficient for a culture to become virus positive.

Following inoculation, the animals were observed daily, and blood samples were obtained every 2 weeks for 8 weeks and at monthly intervals thereafter. Virus isolation attempts were performed by cocultivation of PBMC from each animal with PHA-stimulated normal human PBMC in 25-cm² tissue culture flasks. We also attempted to isolate virus from bone marrow biopsy samples obtained at 3 and 9 months and from lymph node biopsies at 6 and 11½ months after inoculation of Infected PBMC. At 4 weeks after challenge and at every time thereafter, virus was isolated from PBMC, as well as bone marrow and lymph node samples, from the control animal, C-435. In contrast, virus was not isolated at any time from PBMC, nor from bone marrow or lymph node biopsies, from the immunized chimpanzee, C-339. HIV-specific antibodies were detected in serum from C-435 initially at 8 weeks after challenge, and titers continued to rise through week 24 (FIG. 1). However, no anamnestic response was detected in serum from C-339, and antibody titers to HIV-1 diminished slightly, then remained stable.

These results, therefore, indicated that it was possible to prevent transmission of infection by HIV-infected cells by prior immunization. As confirmation, two additional immunized chimpanzees were challenged with an equivalent number of infectious cells using an aliquot of the same cryopreserved PBMC from chimpanzee C-087 (Table 1). One of these chimpanzees, C-499, like C-339, had been immunized and challenged previously with cell-free HIV-1 and had remained virus negative for 1 year ( ). The second chimpanzee, C-447, had been immunized initially with purified recombinant gp160env, p18gag, vif, and nef proteins in SAF-1™, and then received booster immunizations with purified gp160env and p18gag, followed by peptides representing the principal neutralizing determinant (V3 loop) of HIV-1$_{HTLV-IIIB}$ and purified nef protein in SAF-1™. Chimpanzee C-447 had not been exposed previously to infectious HIV-1 in any form.

Following challenge, with the same dose of approximately 22 infectious PBMC, these latter two chimpanzees were monitored biweekly, then monthly, for changes in HIV-specific antibody titers and for presence of virus in PBMC, bone marrow and lymph node. Antibody titers to HIV-1 in both animals remained stable, and virus was not isolated from any of the blood or tissue samples. At 7 months after challenge, C-499 was sacrificed due to congestive heart failure. Fragments of eight different tissues (including brain, spleen, various lymph nodes, kidney, liver and salivary gland) were minced with scissors; these tissue fragments, as well as PBMC and bone marrow, were then cocultivated with PHA-stimulated normal human PBMC. All cultures were virus negative throughout 6 weeks in culture, as monitored by reverse transcriptase assay. All PBMC, bone marrow and lymph node samples from the second animal, C-447, have been negative for virus on all attempts through 9 months of follow-up. Thus, three of three immunized chimpanzees were apparently protected from infection by HIV-1-infected cells. Since peripheral blood cells contain monocyte/macrophages as well as lymphocytes, the infected cell population was probably heterogeneous not only with respect to cell type but also according to levels of virus expression by individual cells. Although the inocula was prepared as PBMC suspended in 1 ml of medium, it is highly likely that some of C-087's PBMC were actively producing HIV. It is possible, therefore, that the chimpanzee inocula actually consisted of a mixture of both cell-free and cell-associated HIV-1. These considerations further enhance the importance of our results.

At time of challenge with HIV-infected PBMC, C-447 and C-499 had fourfold lower HIV-1 EIA antibody titers (1:6400 versus 1:25,600), but four- to eight-fold higher neutralizing antibody titers (1:256 and 1:512 versus 1:64), compared with those of C-339. To assess further the potential of the in vitro serum and PBMC inhibition assays to predict possible vaccine-induced protection against cell-associated virus challenge, serum samples from C-447 and C-499 were tested. Serum obtained from C-447 and C-499 on day of challenge inhibted cell-to-cell transmission of HIV-1 by 25% and 52%, respectively. Because these levels of inhibition were less than the 75% inhibition of cell-to-cell transmission observed with serum from C-339 on the day it was challenged, this assay may not be a reliable predictor of protection against cell-associated challenge. PBMC from these two chimpanzees on the day of cell-associated challenge were tested in parallel with PBMC from C-339 (see FIG. 2B, week 75). Results were equivalent to those obtained with C-339's PBMC from week 75; that is, PBMC from both animals exhibited no apparent inhibitory activity against transmission of virus from C-087's infected cells.

When C-339 had been protected from cell-associated HIV-1 challenge for 1 year (week 104 relative to the initial cell-free virus challenge of C-339), we again challenged this animal with an inoculum of cell-free HIV-1$_{HTLV-IIIB}$ that was equivalent to that used for the first challenge experiment 2 years earlier. Using another cryopreserved aliquot of the same virus stock (obtained from Larry Arthur, NCI-FCRF), 100 TCID$_{50}$ were injected intravenously in a total volume of 1 ml. HIV-1 was initially detected in PBMC from C-339 (by cocultivation with normal human PBMC) that were obtained 4 weeks after this third HIV-1 challenge, and an increase in HIV-1 EIA antibody titer was observed at 6 weeks after challenge (FIG. 1, week 110). Because C-339 had not received a booster immunization or been exposed to HIV-1 for 1 year prior to this second challenge with cell-free HIV-1, the immune response elicited by vaccination did not persist at a level sufficient to protect against this last exposure to virus. C-339 became infected despite the presence of a stable HIV-1 immune response, and infection was detected relatively soon after the third exposure to virus. This finding shows that C-339 was not inherently resistant to HIV-1 infection, and furthermore, underscores the significance of the observed protection against cell-associated HIV-1 challenge. The other surviving chimpanzee, C-447, will be challenged similarly when it has remained virus negative for 1 year.

The mechanism of protection of the three chimpanzees against challenge with HIV-infected cells is not known, but it is likely to be due to a combination of both humoral and cell-mediated immunity. In the in vitro assays with PBMC obtained on the days of challenge, only cells from C-339, but not from C-499 and C-447, exhibited significant inhibitory activity against recovery of HIV-1 from C-087's PBMC. This may have resulted from the fact that C-339 was boosted with multiple HIV-1 antigens 4 and 8 weeks prior to cell challenge, whereas C-499 had not been exposed to HIV-1 antigens for more than 1 year Also, C-447 had received three booster immunizations with only V3 peptides and Nef protein during an interval 2 to 5 months earlier; these inoculations had resulted in more than a tenfold increase in neutralizing antibody titers, but no detectable increase in HIV-specific EIA antibody titers. That PBMC from C-339 subsequently lost the ability to prevent cell-to-cell transmissions in vitro supports this possibility. Irrespective of this, it appears that neither of the in vitro assays, as performed with serum or PBMC, are predictive of protective immunity.

Because C-087 and the three chimpanzees that were challenged with HIV-infected PBMC from C-087 were not siblings, the possibility that the four animals shared identical major histocompatibility complex (MHC) haplotypes is extremely low. Thus, one would assume a priori that initial protection against C-087's PBMC, some of which had HIV antigens on their surface, was not mediated by classical MHC-restricted cytotoxic T-cell activity, even if present. To date we have boen unable to detect CTL activity directly in peripheral blood lymphocytes from immunized chimpanzees ( ). The most likely cell-mediated mechanism of protection would appear to be antibody-dependent cellular cytotoxicity (ADCC), an activity previously detected in serum from C-339 ( ). As indicated above, it is likely that both HIV-specific antibodies and cell-mediated activities synergized to effect protection.

Ideally, a vaccine against any pathogen should be one that elicits long-lasting immunity following a minimal number of immunizations. While we have observed long-lasting, stable EIA and neutralizing antibody titers in our immunized chimpanzees, these were achieved with a large number of immunizations (no fewer than ?12?) over a minimum of 2 years. These regimens, to say the least, are not practical for use in Western nations, much less in developing countries. Based on studies to date in nonhuman primate models, it appears as though immunization against HIV-1 will require at least three inoculations initially and booster inoculations at unspecified intervals. If multiple inoculations are required, then they must be easily administered (such as orally), and the vaccine preparation must be stable under normal storage conditions. These latter two conditions are especially important relative to HIV-1 vaccine delivery to developing nations. Thus, although progress has been made to demonstrate that it is possible to elicit protection against intravenous infection with both cell-free and cell-associated HIV-1, major problems remain to be resolved.

TABLE 1

Immunization history of chimpanzees prior to challenge with HIV-infected cells.

| | Chimpanzees | | | |
|---|---|---|---|---|
| | C-339 | C-435 | C-499 | C-447 |
| Immunization: | inactivated HIV gp160, V3-KLH | none | gp160, p18 21 V3 pept | gp160, p18 vif, nef, V3 |
| Prior challenge with cell-free HIV-1: Status at time of cell-associated challenge: | yes | no | yes | no |
| EIA anti-HIV titer: | 25,600 | <100 | 6,400 | 6,400 |

TABLE 1-continued

Immunization history of chimpanzees prior to challenge with HIV-infected cells.

| | Chimpanzees | | | |
|---|---|---|---|---|
| | C-339 | C-435 | C-499 | C-447 |
| Neutralizing titer: | 1:64 | <4 | 1:512 | 1:256 |
| Virus recovery: | none | wk 4 | none | none |

Serum Neutralization of Cell-to-Cell Transmission

| Chimpanzee | Serum date | % Inhibition |
|---|---|---|
| C-339 | 10/87 | 0 |
| Roberta | 3/88 | 98 |
| C-339 | 8/89 | 68 |
| | 1/90 | 34 |
| | 8/90 | 75 |
| C-499 | 1/90 | 18 |
| | 7/90 | 49 |
| | 1/91 | 52 |
| C-447 | 1/89 | 12 |
| | 10/90 | 27 |
| | 1/91 | 25 |
| C-433 | 8/89 | 35 |

$6 \times 10^5$ PBMC from C-527, 4 mos. p.i.
Average of 3 experiments

REFERENCES

1. Koff, W. C. & Fauci, A. S. (1989) *AIDS* 3(S1), S125–S129.

2. Ada, G. L. (1989) *Nature* (London) 339, 331–332.

3. Berman, P. W., Groopman, J. E., Gregory, T., Clapham, P. R., Weiss, R. A., Ferriani, R. Riddle, L., Shimasaki, C., Lucas, C., Lasky, L. A. & Eichberg, J. W. (1988) *Proc. Natl. Acad. Sci. U.S.A.* 85 5200–5204.

4. Arthur, L. O., Bess, J. W., Waters, D. J., Pyle, S. W., Kelliher, J. C., Nara, P. L., Krohn, K., Robey, W. G., Langlois, A. J., Gallo, R. C. & Fischinger, P. J. (1989) *J. Virol.* 63,5046–5053.

5. Girard, M., Kieny, M. P., Gluckman, J. C., Barre-Sinoussi, F., Montagnier, L. & Fultz, P. (1990) in *Vaccines for Sexually Transmitted Diseases* eds. Meheus, A. & Spier, R. (Butterworth Co., Ltd., London), pp. 227–237.

6. Hu, S. L. Fultz, P. N., McClure, H. M., Eichberg, J. W., Thomas, E. K., Zarling, J., Singhal, M. C., Kosowski, S. G., Swenson, R. B., Anderson, D., C. & Todaro, G. (1987) *Nature* (London) 328, 721–723.

7. Berman, P. W., Gregory, T. J., Riddle, L., Nakamura, G. R., Champe, M. A., Porter, J. P., Wurm, F. M., Hershberg, R. D., Cobb, E. K. & Eichberg, J. W. (1990) *Nature* (London) 345, 622–625.

8. Desrosiers, R. C., Wyand, M. S., Kodama, T., Ringler, D. J., Arthur, L. O., Sehgal, P. K., Letvin, N. L., King, N. W. & Daniel, M. D. (1989) *Proc. Natl. Acad. Sci. U.S.A.* 86 86, 6353–6357.

9. Murphey-Corb, M., Martin, L. M., Davison-Fairburn, B., Montelaro, R. C., Miller, M., West, M., Ohkawa, S., Baskin, G. B., Zhang, J. Y., Putney, S., D. Allison, A. C. & Eppstein, D. A. (1989) *Science* 246, 1293–1297.

10. Emini, E. A., Nara, P. L., Schleif, W. A., Lewis, J. A., Davide, J. P., Lee, D. R., Kessler, J., Conley, S., Matsushita, S., Putney, S. D., Gerety, R. J. & Eichberg, J. W. (1990) *J. Virol.* 64, 3674–3678.

11. Moor-Jankowski, J. & Mahoney, C. J. (1989) *J. Med. Primatol.* 18, 1–26.

12. Kieny, M. P., Lathe R., Riviere, Y., Dott, K., Schmitt, D., Girard, M., Montagnier, L. & Lecocq. J. P. (1988) *Prot. Engineering* 2, 219–226.

13. Schmidt, D., Dezutter-Dambuyant, C., Hanau, D., Schmitt, D. A., Kolbe, H. V. J., Kieny, M. P., Cazenave, J. P. & Thivolet, J. (1989) *Comptes Rendus Acad. Sci. Paris*, 308(III), 269–275.

14. Guy, B., Riviere, Y., Dott, K. Regnault, A. & Kieny, M. P. (1990) *Virology* 176, 413–425.

15. Kolbe, H. V., Jaeger, F., Lepage, P., Roitsch, C., Lacaud, G., Kieny, M. P., Sabatie, J., Brown, S. W. & Lecocq, J. P. (1989) *J. Chromatography* 476, 99–112.

16. Allison, A. C. & Byars, N. E. (1986) *J. Immunol. Methods* 95, 157–168.

17. Putney, S. D., Matthews, T. J., Robey, W. G., Lynn, D. L., Robert-Guroff, M., Mueller, W. T., Langlois, A. L., Ghrayeb, J., Petteway, S. R., Weinhold, K. J., Fischinger, P. J., Wong-Staal, F., Gallo, R. C. & Bolognesi, D. P. (1986) *Science* 234, 1392–1395.

18. Rusche, J. R., Kavaherian, K., McDanal, C., Petro, J., Lynn, D. L., Grimaila, R., Langlois, A., Gallo, R. C., Arthur, L. O., Fischinger, P. J., Bolognesi, D. P., Putney, S. D. & Matthews, T. J. (1988) *Proc. Natl. Acad. Sci. U.S.A.* 85, 3198–3202.

19. LaRosa, G. J., Davide, J. P., Weinhold, K., Waterbury, J. A., Profy, A. T., Lewis, J. A., Langlois, A. J., A. J., Dressman, G. R. Boswell, R. N., Shadduck, P., Holley, L. H., Karplus, M., Bolognesi, D. P., Matthews, T. J. Emini, E. A. & Putney, S. D. (1990) *Science* 249 932–935.

20. Nara, P. L., Hatch, W. C., Dunlop, N. M., Robey, W. G., Arthur, L. O., Gonda, M. A. & Fischinger, P. J. (1987) *AIDS Res. Human Retroviruses* 3, 283–302.

21. Fultz, P. N., McClure, H. M., Swenson, R. B., McGrath, C. R., Brodie, A., Getchell, J. P., Jensen, F. C., Anderson, D. C., Broderson, J. R. & Francis, D. P. (1986) *J. Virol.*, 58, 116–124.

22. Laure, F., Rouzioux, C., Veber, F., Jacomet, C., Courgnaud, V., Blanche, S., Burgard, M., Griscelli, C. & Brechot, C. (1988) *Lancet* 2, 538–541.

23. Mullis, K. B. & Faloona, F. A. (1987) *Methods Enzymol.* 155, 335–350.

24. Kwok, S. & Kellogg, D. E. (1990) in *PCR Protocols: A Guide to Methods and Applications*: eds. Innis, M. A., Gelfand, D. H., Sninsky, J. J. & White T. J. (Academic Press, Inc., San Diego, Calif.) pp. 337–347.

25. Zagury, D., Bernard, J., Cheynier, R., Desportes, I., Leonard, R., Fouchard, M., Reveil, B., Ittele, F. D., Lurhama, Z., Mbayo, K., Wane, J., Salaun, J. J., Goussard, B., Dechazal, L., Burny, A., Nara, P. & Gallo, R. C. (1988) *Nature* (London) 322, 728–731.

26. Nara, P. L., (1989) in *Vaccines* 89, eds. Lerner, R. A., Ginsberg, H., Chanock, R. M. & Brown, F. (Cold Spring Harbor Laboratory, Cold Spring Harbor, N.Y.) pp. 137–144.

27. Myers, G. (1990) in *Human Retroviruses and AIDS*, eds. Myers, G., Josephs, S. F., Wong-Staal, F., Rabson, A. B., Smith, T. F. & Berzofsky, J. A. (Los Alamos National Laboratory, Los Alamos, N.Mex.).

28. Scharf, S. J., Horn, G. T. & Erlich, H. A. (1986) *Science* 233, 1076–1078.

29. Walker, C. M., Moody, D. J., Stites, D. P. & Levy, J. A. (1986) *Science* 234, 1563–1566.

30. Tsubota, H., Lord, C. I., Watkins, D. I., Morimoto, C. & Letvin, N. L. (1989) *J. Exp. Med.* 169, 1421–1434.

31. Ranki, A., Valle, S. L., Krohn, M., Antonen, J., Allain, J. P., Leuther, M., Franchini, G. & Krohn, K. (1987) *Lancet* 2, 589–593.

32. Jehuda-Cohen, T., Slade, B. A., Powell, J. D., Villinger, F., De, B., Folks, T. M., McClure, H. M., Sell, K. W. & Ahmed-Ansari, A. (1990) *Proc. Natl. Acad. Sci. U.S.A.* 87, 3972–3976.

33. Bahraoui, E., Yagello, M., Billaud, J. N., Sabatier, J. M., Guy, B., Muchmore, E., Girard, M. & Gluckman, J. C. (1990) *AIDS Res. Human Retroviruses* 6, 1087–1088.

34. Van Eendenburg, J. P., Yagello, M., Girard, M., Kieny, M. P., Lecocq, J. P., Muchmore, E., Fultz, P. N., Riviere, Y., Montagnier, L. & Gluckman, J. C. (1989) *AIDS Res. Human Retroviruses* 5, 41–50.

---

I claim:

1. A method of enhancing the immunogenicity of an envelope glycoprotein of HIV-1, wherein the method comprises administering to a host at least one envelope glycoprotein of HIV-1 in an amount sufficient for priming vaccination and at least one major neutralization peptide from the V3 loop of HIV-1, wherein the peptide is administered to the host in an amount sufficient to enhance the induction of neutralizling antibodies in the host and to confer to the host long-lasting immnunity against HIV-1 as evidenced by unisolatable virus for up to one year.

2. The method of claim 1, wherein said at least one protein is the gag protein.

3. The method of claim 1, wherein said at least one protein are the gag, vif, and nef proteins.

4. Method as claimed in claim 1, wherein said envelope glycoprotein and said peptide are simultaneously administered to said host.

5. Method as claimed in claim 1, wherein said envelope glycoprotein is gp120 or gp160 of HIV-1.

6. Method as claimed in claim 1, wherein the envelope glycoprotein is orally administered to the host.

7. Method as claimed in claim 1, wherein the envelope glycoprotein is parenterally administered to the host.

8. Method as claimed in claim 1, wherein the peptide is orally administered to the host.

9. Method as claimed in claim 1, wherein the peptide is intradermally administered to the host.

10. Method as claimed in claim 1, wherein said envelope glycoprotein is gp120 of HIV-1.

11. Method as claimed in claim 1, wherein the envelope glycoprotein and the peptide are administered in combination with an adjuvant to the host.

12. Method as claimed in claim 11, wherein the adjuvant is muramyl dipeptide in a lipid medium or incomplete Freund's adjuvant.

13. Method as claimed in claim 1, wherein at least one peptide of HIV-1 is administered to said host along with said at least one major neutralization peptide from the V3 loop, wherein said peptide of HIV-1 is selected from the group consisting of env, pol, gag, nef, vif peptides of HIV-1, and mixtures of said peptides of HIV-1.

14. Method as claimed in claim 12, wherein the major neutralization peptide is selected from the group consisting of:

C-TRPNNNTRKR IRIQRGPGRA FVTIGK-IGN M-RQAH-C,
C-TRPNNNTRKS IRIQRGPGRA FVTIGK-IGN M-RQAH-C,
C-TRPNNNTRKK IRIQRGPGRA FVTIGK-IGN M-RQAH-C,
C-TRPNNNTRGS IRIQRGPGRA FVTIGK-IGN M-RQAH-C,
C-TRPNNNTRKS IYI--GPGRA FHTTGRIIGD-IRKAH-C,
C-TRPYNNVRRS LSI--GPGRA FRTRE-IIGI -IRQAH-C,
C-TRPGNNTRRG IHF--GPGQA LYTTGIV-GD-IRRAY-C,
C-ARPYQNTRQR TPI--GLGQS LYTTRSR-SI-IGQAH-C,
C-TRPNNNTRKS ITK--GPGRV IYATGQIIGD-IRKAH-C,
C-TRPNNNTRKR ITM--GPGRV YYTTGQIIGD-IRRAH-C,
C-TRPGSDKRQS TPI--GLGQA LYTTRGRTKI-IGQAH-C,
C-TRPGSDKKIR QSIRIGPGKV FYAKGG---I-TGQAH-C,
C-TRPNNNTKKG IAI--GPGRT LYAREKIIGD-IRQAH-C,
C-TRPNNHTRKR VTL--GPGRV WYTTGEILGN-IRQAH-C,
C-TRPGNNTRRG SHF--GPGQA LYTTGIVGDI-RRAY-C,
C-TRPDNKITSRQ-TPI -GLGQA LYTTRIKGDI-RQAY-C,
C-TRPNNNVRRR-HIHI-GPGRA FYTGEIRNI-RQAH-C,
C-TRPYKNTRQS-TPI-GLGQA LYTTHTKSI-GQAH-C,
C-TRPNNNTTRS-IHI--GPGRA FYATGDIIGTIRQAH-C, and
C-TRPNYNKRKR-IHI--GPGRA FYTTKN-IIGDIRQAH-C.

15. Method as claimed in claim 12, wherein the peptide comprises the following amino acid sequence:
YNTRKSIRIQRGPGRAFVTIGKIGN.

16. Method as claimed in claim 12, wherein said envelope glycoprotein is administered to said host, wherein said at least one major neutralization peptide is administered to said host after said envelope glycoprotein, and wherein thereafter a mixture comprising at least one envelope glycoprotein of HIV-1 and at least one major neutralization peptide is administered to said host.

17. Method as claimed in claim 16, wherein said envelope glycoprotein is gp160 of HIV-1.

18. Method as claimed in claim 1, wherein said envelope glycoprotein is gp160 of HIV-1.

19. Method as claimed in claim 1, wherein said envelope glycoprotein is administered to said host, and then said peptide is administered to said host.

20. A composition for enhancing the immunogenicity of an envelope glycoprotein of HIV-1 BRU, wherein the composition comprises, as a combined preparation for simultaneous, separate, or sequential use:

(A) at least one envelope glycoprotein of HIV-1 BRU; and
(B) at least one peptide derived from the amino acid sequence of the envelope glycoprotein;

wherein the envelope glycoprotein is administered in an amount sufficient for priming vaccination, and the peptide is administered in an amount sufficient to enhance induction of neutralizing antibodies in the host and to confer long-lasting immunity against HIV-1 as evidenced by unisolatable virus for up to one year.

21. A composition as claimed in claim 20, wherein the envelope glycoprotein is gp160 of HIV-1 or gp120 of HIV-1.

22. Composition as claimed in claim 20, wherein the composition is suitable for oral, parenteral, or intradermal administration.

23. Composition as claimed in claim 20, wherein the envelope glycoprotein is combined with a pharmaceutical vehicle for oral or parenteral administration.

24. Composition as claimed in claim 20, wherein the peptide is combined with a pharmaceutical vehicle for oral administration.

25. Composition as claimed in claim 20, wherein at least one of said at least one envelope glycoprotein of the virus and said at least one major neutralization peptide is presented:
either as particles, or by a live recombinant microorganism.

26. The composition of claim 20, further comprising at least one protein of HIV-1 selected from the group consisting of the nef vif, pol, and gag proteins.

27. The composition of claim 26, wherein said at least one protein is the gag protein.

28. The composition of claim 26, wherein said at least one protein are the gag, vif, and nef proteins.

29. Composition as claimed in claim 20, wherein the peptides are bound to a carrier therefor.

30. Composition as claimed in claim 20, further comprising the adjuvant muramyl dipeptide or incomplete Freund's adjuvant.

31. Composition as claimed in claim 20, wherein in addition to said major neutralization peptide, the composition further comprises at least one peptide of HIV-1 selected from the group consisting of env, pol, gag, nef, vif peptides of HIV-1, and mixtures of said peptides of HIV-1.

32. Composition as claimed in claim 31, wherein the major neutralization peptide is at least one peptide selected from the group consisting of:

C-TRPNNNTRRKR IRIQRGPGRA FVTIGK-IGN M-RQAH-C,
C-TRPNNNTRKS IRIQRGPGRA FVTIGK-IGN M-RQAH-C,

C-TRPNNNTRKK IRIQRGPGRA FVTIGK-IGN M-RQAH-C,

C-TRPNNNTRGS IRIQRGPGRA FVTIGK-IGN M-RQAH-C,

C-TRPNNNTRKS IYI--GPGRA FHTTGRIIGD-IRKAH-C,

C-TRPYNNVRRS LSI--GPGRA FRTRE-IIGI -IRQAH-C,

C-TRPGNNTRRG IHF--GPGQA LYTTGIV-GD-IRRAY-C,

C-ARPYQNTRQR TPI--GLGQS LYTTRSR-SI-IGQAH-C,

C-TRPNNNTRKS ITK--GPGRV IYATGQIIGD-IRKAH-C,

C-TRPNNNTRKR ITM--GPGRV YYTTGQIIGD-IRRAH-C,

C-TRPGSDKRQS TPI--GLGQA LYTTRGRTKI-IGQAH-C,

C-TRPGSDKKIR QSIRIGPGKV FYAKGG---I-TGQAH-C,

C-TRPNNNTKKG IAI--GPGRT LYAREKIIGD-IRQAH-C,

C-TRPNNHTRKR VTL--GPGRV WYTTGEILGN-IRQAH-C,

C-TRPGNNTRRG SHF--GPGQA LYTTGIVGDI-RRAY-C,

C-TRPDNKITSRQ-TPI-GLGQA LYTTRIKGDI-RQAY-C,

C-TRPNNNVRRR-HIHI-GPGRA FYTGEIRNI-RQAH-C,

C-TRPYKNTRQS-TPI--GLGQA LYTTRTKSI -GQAH-C,

C-TRPNNNTTRS-IHI--GPGRA FYATGDIIGTIRQAH-C, and

C-TRPNYNKRKR-IHI--GPGRA FYTTKN-IIGDIRQAH-C.

33. Composition as claimed in claim 31, wherein the peptide comprises the following amino acid sequence:

YNTRKSIRIQRGPGRAFVTIGKIGN.

* * * * *

UNITED STATES PATENT AND TRADEMARK OFFICE
CERTIFICATE OF CORRECTION

PATENT NO. : 5,876,724
DATED : March 2, 1999
INVENTOR(S) : Marc Girard

It is certified that error appears in the above-identified patent and that said Letters Patent is hereby corrected as shown below:

Column 4, line 47, insert the following:

--FIG. 12 depicts the immunization history of chimpanzees prior to challenge with HIV-1 infected cells.
   FIG. 13 depicts HIV-1-specific antibody titers in serum from C-339 and C-435.
   FIGS. 14A and 14B depict serum neutralization of cell-to-cell transmission of HIV-1.--

Column 25, line 50, after "antigens" insert --(FIG. 12)--.

Column 26, line 3, change "(FIG. 1)" to --(FIG. 13)--.

Column 26, lines 20 and 21, change "(FIG. 2A)" to --(FIG. 14A)--.

Column 26, line 45, delete "(FIG. 2B)".

Column 26, line 48, delete "(FIG. 2C)".

Column 27, line 30, change "(FIG. 1)" to --(FIG. 13)--.

UNITED STATES PATENT AND TRADEMARK OFFICE
CERTIFICATE OF CORRECTION

PATENT NO. : 5,876,724

DATED : March 2, 1999

INVENTOR(S) : Marc Girard

It is certified that error appears in the above-identified patent and that said Letters Patent is hereby corrected as shown below:

Column 27, line 38, change "(Table 1)" to --(FIG. 12)--.

Column 28, line 23, after "respectively" insert --(FIG. 14B)--.

Column 28, lines 29 and 30, delete "(see FIG. 2B, week 75)".

Column 28, line 46, change "(FIG. 1, week 110)" to --(FIG. 13, week 110)--.

Signed and Sealed this

Thirteenth Day of July, 1999

*Attest:*

Q. TODD DICKINSON

*Attesting Officer*  Acting Commissioner of Patents and Trademarks